United States Patent
Nagata et al.

(10) Patent No.: US 9,011,888 B2
(45) Date of Patent: Apr. 21, 2015

(54) ORGANIC-INORGANIC COMPOSITE PARTICLES, PROCESS FOR PRODUCING THE SAME, DISPERSION CONTAINING THE PARTICLES, AND COSMETIC CONTAINING THE PARTICLES

(75) Inventors: Kensuke Nagata, Kitakyushu (JP); Michio Komatsu, Kawasaki (JP)

(73) Assignee: JGC Catalysts and Chemicals Ltd., Kawasaki-shi (JP)

( * ) Notice: Subject to any disclaimer, the term of this patent is extended or adjusted under 35 U.S.C. 154(b) by 143 days.

(21) Appl. No.: 13/388,711

(22) PCT Filed: Jul. 30, 2010

(86) PCT No.: PCT/JP2010/062958
§ 371 (c)(1),
(2), (4) Date: Feb. 3, 2012

(87) PCT Pub. No.: WO2011/016404
PCT Pub. Date: Feb. 10, 2011

(65) Prior Publication Data
US 2012/0128748 A1   May 24, 2012

(30) Foreign Application Priority Data
Aug. 6, 2009  (JP) ................................ 2009-183914

(51) Int. Cl.
| | |
|---|---|
| A61K 8/02 | (2006.01) |
| A01N 59/00 | (2006.01) |
| A61K 33/00 | (2006.01) |
| C09C 3/10 | (2006.01) |
| A61K 8/73 | (2006.01) |
| A61Q 1/12 | (2006.01) |
| C09C 1/30 | (2006.01) |

(52) U.S. Cl.
CPC ................. *C09C 3/10* (2013.01); *A61K 8/0241* (2013.01); *A61K 8/735* (2013.01); *A61K 2800/412* (2013.01); *A61K 2800/614* (2013.01); *A61Q 1/12* (2013.01); *C01P 2004/03* (2013.01); *C09C 1/3072* (2013.01)

(58) Field of Classification Search
None
See application file for complete search history.

(56) References Cited

U.S. PATENT DOCUMENTS

| | | | |
|---|---|---|---|
| 4,500,676 A * | 2/1985 | Balazs et al. | ............... 428/425.1 |
| 5,091,013 A | 2/1992 | Miyoshi et al. | |
| 5,118,727 A * | 6/1992 | Roberts et al. | ................ 523/216 |

(Continued)

FOREIGN PATENT DOCUMENTS

| | | |
|---|---|---|
| EP | 2033619 A1 | 3/2009 |
| JP | 62169712 A | 7/1987 |

(Continued)

*Primary Examiner* — Trevor Love
(74) *Attorney, Agent, or Firm* — The Webb Law Firm

(57) ABSTRACT

Organic-inorganic composite particles includes inorganic oxide particles each of which has a cationic charge on the particle surface and polymer gel molecules which are derived from a natural substance, have an anionic functional group and one or more hydroxyl groups in a molecule and have both a shrinking and a swelling property, the polymer gel molecules are electrostatically bonded to surfaces of the inorganic oxide particles; a process for producing the particles; a dispersion containing the particles; and a cosmetic containing the particles. These organic-inorganic composite particles have good dispersibility not only in aqueous solvents such as water but also in non-aqueous solvents and further have characteristics that aggregation of the particles scarcely occurs.

8 Claims, 1 Drawing Sheet

(56) References Cited

U.S. PATENT DOCUMENTS

| | | |
|---|---|---|
| 5,871,872 A | 2/1999 | Matijevic et al. |
| 7,501,136 B2 | 3/2009 | Hagura et al. |
| 2004/0197359 A1 | 10/2004 | Yamada et al. |
| 2006/0034879 A1 | 2/2006 | Miyazaki et al. |
| 2006/0039986 A1 | 2/2006 | Okamoto et al. |
| 2006/0040892 A1* | 2/2006 | Hu et al. ............ 514/54 |
| 2007/0167562 A1* | 7/2007 | Zhou et al. .......... 524/565 |
| 2009/0191246 A1 | 7/2009 | Miyazaki et al. |

FOREIGN PATENT DOCUMENTS

| | | |
|---|---|---|
| JP | 62209011 A | 9/1987 |
| JP | 63199273 A | 8/1988 |
| JP | 3153612 A | 7/1991 |
| JP | 10251122 A | 9/1998 |
| JP | 11166127 A | 6/1999 |
| JP | 2002255744 A | 9/2002 |
| JP | 2003012460 A | 1/2003 |
| JP | 2003063932 A | 3/2003 |
| JP | 2005126426 A | 5/2005 |
| JP | 2006045491 A | 2/2006 |
| JP | 2006052299 A | 2/2006 |
| JP | 2007284483 A | 11/2007 |
| JP | 2008007536 A | 1/2008 |
| JP | 2009143825 A | 7/2009 |
| JP | 2009155211 A | 7/2009 |

* cited by examiner

ORGANIC-INORGANIC COMPOSITE PARTICLES, PROCESS FOR PRODUCING THE SAME, DISPERSION CONTAINING THE PARTICLES, AND COSMETIC CONTAINING THE PARTICLES

TECHNICAL FIELD

The present invention relates to organic-inorganic composite particles wherein polymer gel molecules derived from a natural substance and having an anionic functional group and one or more hydroxyl groups in a molecule are electrostatically bonded to particle surfaces, a process for producing the particles, a dispersion containing the particles and a cosmetic containing the particles.

BACKGROUND ART

Inorganic oxide particles are used by adding them for purposes of pigments, ultraviolet light absorbers, fillers of coating materials, inks, resin compositions, cosmetics, and the like. On the surfaces of such inorganic oxide particles, however, hydroxyl groups are present, and therefore, they have low dispersibility in low-polarity solvents such as oils having poor affinity with water, so that there is a problem that aggregation of the particles is liable to occur.

As a means to solve such a problem, the present applicant has studied, for example, a process for producing resin-coated particles using porous silica particles. In patent literature 1, the present applicant has disclosed an emulsion process or a polymerization process.

Further, the present applicant has described, in patent literature 2, a process for producing resin-coated particles by plasma polymerization. Moreover, the present applicant has disclosed, in patent literature 3, a process for producing resin-coated particles by spray drying of scale-like composite particles.

In the case where polymer gel molecules derived from a natural substance are used for cosmetics, a polymer gel solution is used as it is in most cases, and there are instances where the polymer gel molecules are used as organic particles (including an instance where they are used in combination with organic particles), but there are few instances where they are used in combination with inorganic particles. In patent literature 4, it is described that the polymer gel molecules are stirred in the presence of inorganic pigments, micas, clays, other extender pigments or pigments for cosmetics or industry, and metal (Al, Mg, Ca, Zn, Zr or Ti) salts of polymer substances having a carboxyl group and having an acid value of not less than 200, or the metal salts and a hydrophobing agent and then dried to allow the polymer gel molecules to adhere to the pigments.

On the other hand, in patent literature 5, it is described that natural organic component-supported particles, which are obtained by mixing inorganic particles, such as silicic acid-based compound, alumina-based compound or phosphoric acid-based compound, or organic particles, such as cellulose, with a natural organic component selected from catechins, vitamins, tannins, natural moisture retention factors and essential oils derived from plants and then spray-drying the mixture using a spray dryer, are employable as cosmetic materials because they have dispersibility in linseed oil.

In patent literature 6, a production process in which a moisture-absorbing substance is allowed to adhere to a surface of a pigment is disclosed.

CITATION LIST

Patent Literature

Patent literature 1: Japanese Patent Laid-Open Publication No. 012460/2003
Patent literature 2: Japanese Patent Laid-Open Publication No. 063932/2003
Patent literature 3: Japanese Patent Laid-Open Publication No. 052299/2006
Patent literature 4: Japanese Patent Laid-Open Publication No. 199273/1988
Patent literature 5: Japanese Patent Laid-Open Publication No. 045491/2006
Patent literature 6: Japanese Patent Laid-Open Publication No. 284483/2007

The surface treatment method by emulsion or polymerization process described in the patent literature 1 needs to be further developed in achievement of high-density coating of the inorganic oxide particle surfaces.

In the plasma treated solid described in the patent literature 2, the organic compound needs to be exposed to such conditions that the temperature of the solid surface is instantaneously not lower than 100° C.

In the spray drying method in the patent literature 3, preparation using a spray dryer that is operated in an atmosphere of air stream of not lower than 100° C. in the treatment is essential, and there is a possible that uniform coating cannot be made. The coating method in the patent literature 4 is a method in which a pigment and moisture retention component molecules are stirred and then dried to allow the molecules to adhere to the pigment by means of van der Waals force, and there is a possible that uniform coating cannot be made.

The natural organic component-supported particles described in the patent literature 5 are prepared by the use of a spray dryer that is operated in an atmosphere of air stream of not lower than 100° C. However, in the case where the natural organic component to be supported on the particles has insufficient heat stability, this method cannot be adopted, and therefore, a method of modifying the particle surfaces under the low-temperature conditions has been desired.

In the coating method in the patent literature 6, by adding polyvalent metallic ions in the presence of an inorganic oxide pigment and a surface modifier having an anionic functional group, the polyvalent metallic ions serve to connect the inorganic oxide particles with the surface modifier like metallic soap. However, the coating by these conventional methods of adhesion and spray drying are due to van der Waals force, and there is a problem that the connected organic molecular component is separated or broken off from the particles by the surrounding environmental changes, such as pH and impurity ions, or friction among the particles after coating with the organic molecules.

Furthermore, there has been desired establishment of a process for producing organic-inorganic composite particles in which the particle surfaces can be homogeneously modified by a simple means without receiving any restriction on the component supported on the particle surfaces or the modification component and the properties of the coating component can be retained for a long time.

SUMMARY OF THE INVENTION

Then, the present inventors have earnestly studied for the purpose of solving such problems as described above. As a result, the present inventors have found that organic-inorganic composite particles in which polymer gel molecules derived from a natural substance and having an anionic functional group and one or more hydroxyl groups in a molecule are electrostatically bonded to surfaces of inorganic oxide particles each having a cationic charge on the particle surface and the inorganic oxide particle surfaces are homogeneously modified can be prepared, and they have accomplished the present invention.

The organic-inorganic composite particles of the present invention are characterized by comprising inorganic oxide particles each of which has a cationic charge on the particle surface and polymer gel molecules which are derived from a natural substance and have an anionic functional group and one or more hydroxyl groups in a molecule, said polymer gel molecules being electrostatically bonded to surfaces of the inorganic oxide particles.

The polymer gel molecules are preferably polymer gel molecules having an anionic functional group and one or more hydroxyl groups in a molecule and having both of shrinking and swelling property.

The inorganic oxide particles are preferably particles of an oxide or a composite oxide of at least one metallic element selected from cesium, magnesium, calcium, barium, cerium, titanium, zirconium, vanadium, iron, zinc, aluminum and silicon (except silicon oxide particles).

The inorganic oxide particles are preferably particles in which surfaces of silicon oxide particles each of which has an anionic charge on the particle surface are coated with an oxide or a composite oxide of at least one metallic element selected from cesium, magnesium, calcium, barium, cerium, titanium, zirconium, vanadium, iron, zinc, aluminum and silicon (except silicon oxide particles). As the inorganic oxide particles for use in the present application, particles having been subjected to surface treatment for the purpose of controlling the quantity of surface charge are more preferably used.

The mean particle diameter of the inorganic oxide particles is preferably in the range of 0.1 to 280 μm.

The polymer gel molecules are preferably polymer gel molecules which are changed in their molecular forms and undergo shrinking or swelling according to a change in the surrounding environment.

The polymer gel molecules are preferably polymer gel molecules having one or more hydroxyl groups in a molecule.

The polymer gel molecules are preferably polymer gel molecules having, in a molecule, at least one anionic functional group selected from the group consisting of carboxyl group, thiol group, sulfone group, sulfine group, sulfene group, phosphonic acid group, phosphinic acid group, phosphenic acid group, phosphoric acid group, hydroximic acid group, hydroxamic acid group, nitrole group, nitrosole group and nitronic acid group.

The polymer gel molecules are preferably polymer gel molecules of at least one kind selected from hyaluronic acids consisting of hyaluronic acid and its salts, amino acid, polyamino acid, pyrrolidonecarboxylic acid or its derivatives, urea or its derivatives, N-acetylglucosamine, animal and plant polysaccharides, coenzyme Q10, rice powder, gelatin, oligosaccharide, monosaccharides, saponins, plant peptide, phospholipid, sericin, chondroitin, ceramide, albumin, collagen, chitin, chitosan, and plant/seaweed extracts.

As the polymer gel molecules, at least one compound selected from natural polymer compounds, itaconic acids and N-isopropylacrylamides, or at least one compound selected from copolymers of the above compounds and ester-based compounds or poly(meth)acrylic acid esters may be used.

The natural polymer compound is preferably at least one compound selected from catechins, vitamins, tannins, polysaccharides, proteins, phospholipids, natural moisture retention factors, alginic acids, polyglutamic acids and polyaspartic acids, or its salt.

The catechins are preferably catechins derived from tea.

The vitamin is preferably at least one kind selected from vitamin, vitamin derivatives and vitamin-like substances having functions close to those of vitamin.

The tannin is preferably at least one kind selected from tannin, tannic acid, pyrogallol, gallic acid and gallic acid esters.

The mean particle diameter of the organic-inorganic composite particles is preferably in the range of 0.1 to 300 μm.

The organic-inorganic composite particles are preferably particles whose mean particle diameter has been controlled by the amount of the polymer gel molecules to be electrostatically bonded to the surfaces of the inorganic oxide particles and the time for swelling the polymer gel molecules.

The process for producing organic-inorganic composite particles of the present invention is a process for producing organic-inorganic composite particles comprising inorganic oxide particles each of which has a cationic charge on the particle surface and polymer gel molecules which are derived from a natural substance, have an anionic functional group and one or more hydroxyl groups in a molecule and have both of shrinking and swelling property, said polymer gel molecules being electrostatically bonded to surfaces of the inorganic oxide particles, said process comprising:

(1) a step wherein a solvent capable of shrinking the polymer gel molecules is added to a solution containing the polymer gel molecules and they are stirred, (2) a step wherein the inorganic oxide particles are added to the solution obtained in the step (1) and they are stirred to electrostatically bond the polymer gel molecules to the surfaces of the inorganic oxide particles, (3) a step wherein a solvent capable of swelling the polymer gel molecules is added to the dispersion obtained in the step (2) and they are stirred to swell the polymer gel molecules having been electrostatically bonded to the surfaces of the inorganic oxide particles, (4) a step wherein the dispersion obtained in the step (3) is filtered to separate a solid component, and (5) a step wherein the solid component obtained in the step (4) is dried.

When the polymer gel molecules are those of hyaluronic acid in the above production process, the solvent added in the step (1) is preferably acetone.

When the polymer gel molecules are those of hyaluronic acid, the solvent added in the step (3) is preferably water.

The organic-inorganic composite particle dispersion of the present invention is preferably a dispersion obtained by dispersing the above-mentioned organic-inorganic composite particles in an amount of 0.001 to 50% by weight, in a solvent selected from oils and fats, waxes, hydrocarbons, fatty acids, alcohols, alkyl glyceryl ethers, esters, polyhydric alcohols, saccharides, silicone oil, crosslinked silicone gel and fluorine oil, or a mixed solvent thereof.

The cosmetic of the present invention is a cosmetic containing the above-mentioned organic-inorganic composite particles in an amount of 0.001 to 40% by weight.

The above-mentioned cosmetic is preferably a skin care cosmetic, a base makeup cosmetic, a cleansing cosmetic or a body care cosmetic.

The organic-inorganic composite particles of the present invention, namely, organic-inorganic composite particles comprising inorganic oxide particles and polymer gel molecules which are derived from a natural substance, have both of shrinking and swelling property and are electrostatically bonded to surfaces of the inorganic oxide particles, have good dispersibility not only in aqueous solvents such as water but also in non-aqueous solvents and have characteristics that aggregation of the particles scarcely occurs.

Differently from the conventional organic-inorganic composite particles using van der Waals force, there is no possible that the connected organic molecular component is easily separated or broken off from the particles.

The polymer gel molecules have characteristics that their mean particle diameter can be controlled by the amount of the polymer gel molecules to be bonded to the surfaces of the inorganic oxide particles and the time for swelling the polymer gel molecules.

According to the process for producing organic-inorganic composite particles of the present invention, the polymer gel molecules, which are derived from a natural substance, have an anionic functional group and one or more hydroxyl groups in a molecule and have both of shrinking and swelling property, can be easily bonded to the surfaces of the inorganic oxide particles each of which has a cationic charge on the particle surface by means of electrostatic attraction under the conditions of ordinary temperature, normal pressure and liquid phase. That is to say, according to the present invention, an operation of heating to 100° C. or higher is unnecessary, and therefore, even if the polymer gel molecules have insufficient heat stability, they can be easily bonded to the surfaces of the inorganic oxide particles.

According to the present invention, further, organic-inorganic composite particles which have good dispersibility not only in aqueous solvents such as water but also in non-aqueous solvents and have characteristics that aggregation of the particles scarcely occurs can be obtained.

Moreover, even if the inorganic oxide particles are inorganic oxide particles (e.g., silicon oxide particles such as silica particles) each of which has an anionic charge on the particle surface, they can be used as the inorganic oxide particles referred to in the present invention by coating their surfaces with an inorganic oxide having a cationic charge.

DETAILED DESCRIPTION OF THE INVENTION

Figure 1:
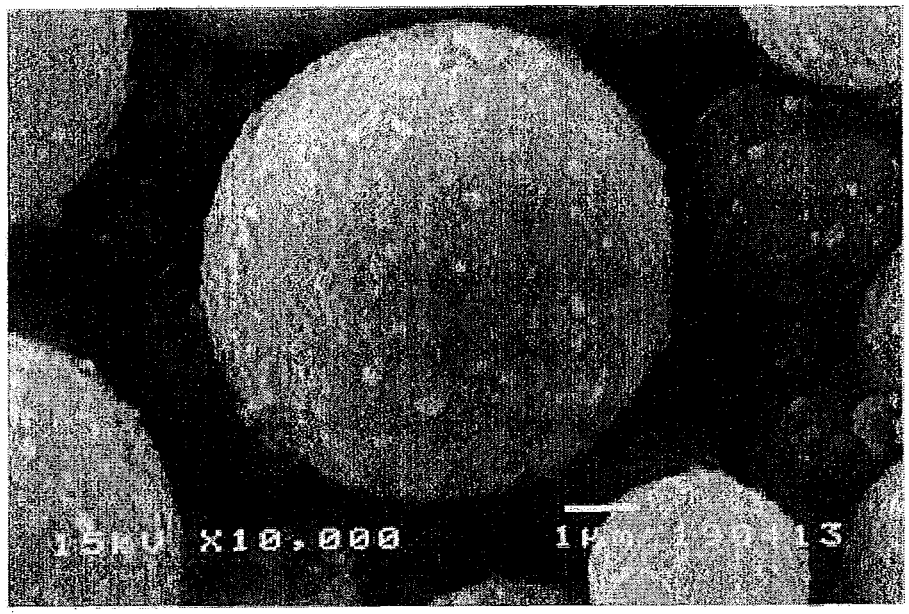
FIG. 1 is a photograph (SEM photograph) of a silica particle coated with alumina (i.e., inorganic oxide particle "alumina-coated silica particle (II)" having cationic charge on the particle surface), said photograph being taken by a scanning electron microscope at a magnification of 10,000.
Figure 2:
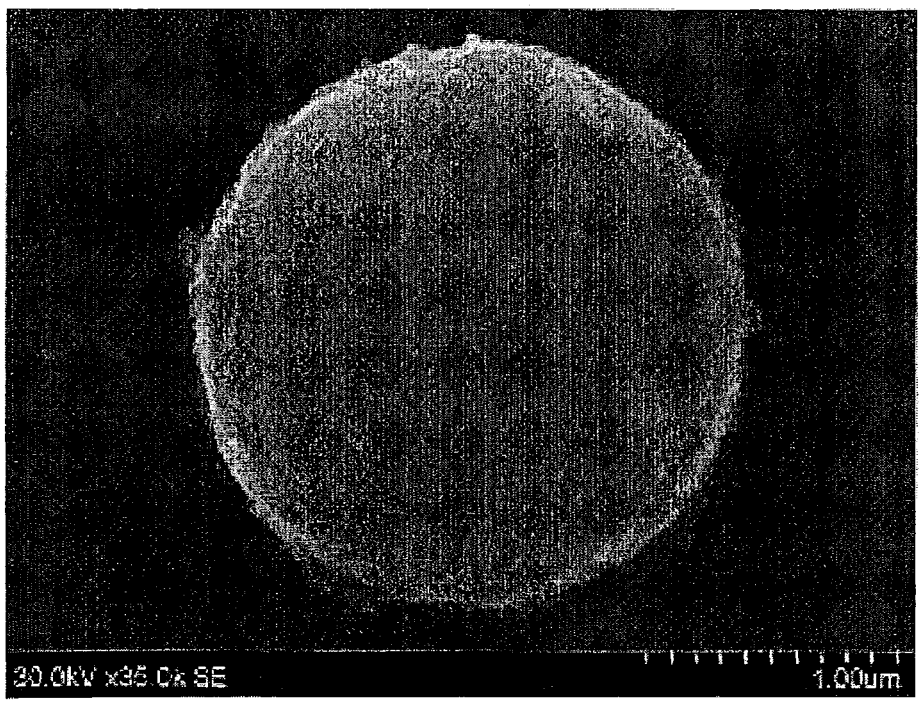
FIG. 2 is a photograph (SEM photograph) of an organic-inorganic composite particle (particle D of Example 4) in which hyaluronic acid is bonded to a surface of a silica particle coated with alumina, said photograph being taken by a scanning electron microscope at a magnification of 350,000.

Embodiments of the organic-inorganic composite particles of the present invention, a process for producing the particles, a dispersion containing the particles and a cosmetic containing the particles are described in detail hereinafter.

Organic-Inorganic Composite Particles

The organic-inorganic composite particles of the present invention are organic-inorganic composite particles comprising inorganic oxide particles each of which has a cationic charge on the particle surface and polymer gel molecules which are derived from a natural substance, have an anionic functional group and one or more hydroxyl groups in a molecule and have both of shrinking and swelling property, said polymer gel molecules being electrostatically bonded to surfaces of the inorganic oxide particles.

Inorganic Oxide Particles

As the inorganic oxide particles, inorganic oxide particles each of which has a cationic charge on the particle surface can be used without any restriction. That is to say, commercially available ones may be used as they are, or inorganic oxide particles prepared by a conventional process may be used. Examples of the preparation processes include spray drying process, hydrolysis process and sol-gel process.

More specifically, the inorganic oxide particles are preferably particles of an oxide or a composite oxide of at least one metallic element selected from cesium, magnesium, calcium, barium, cerium, titanium, zirconium, vanadium, iron, zinc, aluminum, silicon and the like (except silicon oxide particles).

The inorganic oxide particles are preferably particles in which surfaces of silicon oxide particles each of which has an anionic charge on the particle surface are coated with an oxide or a composite oxide of at least one metallic element selected from cesium, magnesium, calcium, barium, cerium, titanium, zirconium, vanadium, iron, zinc, aluminum and silicon (except silicon oxide). The inorganic oxide particles for use in the present invention are more preferably particles having been subjected to surface treatment for the purpose of controlling the quantity of surface charge.

The mean particle diameter of the inorganic oxide particles is preferably in the range of 0.1 to 280 μm, particularly preferably 0.15 to 250 μm. Inorganic oxide particles having a mean particle diameter of less than 0.1 μm are undesirable because the scattering force of particles is increased to make handling of the particles difficult. Inorganic oxide particles having a mean particle diameter of more than 280 μm are undesirable because the spontaneous sedimentation force is increased to make it difficult to homogeneously disperse the particles in a solvent.

The inorganic oxide particles may be those having been subjected to pulverization using a sample mill, a sand mill, a jet mill, a juicer mixer, a Yariya type crusher or the like to adjust their sizes to proper sizes.

The shape of the inorganic oxide particle is not specifically restricted, and a shape that is properly selected from shapes of needle, sphere, rod, plate, scale and circle, hollow and through-hole shape according to the use and effect can be used. With regard to the mean particle diameter, individual measuring conditions (e.g., (length in the lengthwise direction+length in the crosswise direction)/2) are sometimes presented depending upon the shape of the particle, but in the present invention, the mean particle diameter means a value measured by the use of a centrifugal sedimentation type particle size distribution measuring device described in the later-described "Measuring method and evaluation method".

The inorganic oxide particles are usually used after they are added, as they are, to the later-described solution containing organic compound molecules, but particles having a small mean particle diameter (e.g., less than 1 μm) are sometimes aggregated with one another. Therefore, particles having a small mean particle diameter as above are preferably dispersed or suspended in a solvent such as water or an organic solvent, prior to use.

Polymer Gel Molecules

The polymer gel molecules for use in the present invention are polymer gel molecules which are derived from a natural substance, have an anionic functional group and one or more hydroxyl groups in a molecule and have both of shrinking and swelling property, and can be electrostatically bonded to particle surfaces.

The "electrostatic bond" referred to herein means a force acting between a positive charge and a negative charge, such as Coulomb's force, hydrogen bonding force or hydrophobic interaction, and means such a state that the polymer gel molecules are bonded to the surfaces of the inorganic oxide particles by means of electrostatic attraction. Accordingly, such electrostatic bond is distinguished from bond with a weak force, such as van der Waals force or intercalation.

The polymer gel molecules are properly selected from polymer gel molecules which are changed in their molecular forms and undergo shrinking or swelling according to a change in the surrounding environment.

The polymer gel molecules are preferably those having one or more hydroxyl groups in a molecule. By virtue of the hydroxyl groups, the polymer gel molecules incorporate or release water molecules. By the change of an uptake of the water molecules, the polymer gel molecules undergo a change in molecular forms, such as shrinking or swelling.

The polymer gel molecules are preferably polymer gel molecules having, in a molecule, at least one anionic functional group selected from the group consisting of carboxyl group, thiol group, sulfone group, sulfine group, sulfene group, phosphonic acid group, phosphinic acid group, phosphenic acid group, phosphoric acid group, hydroximic acid group, hydroxamic acid group, nitrole group, nitrosole group and nitronic acid group.

More specifically, as the polymer gel molecules, there can be mentioned organic carbon oxide having carboxyl group (—COOH), organic sulfur oxide having thiol group (—SH), sulfone group (—SO$_3$H), sulfine group (—S(=O)OH), sulfene group (—SOH) or the like, organic phosphorus oxide having phosphonic acid group (—P (=O) (OH)$_2$), phosphinic acid group, phosphenic acid group or the like, organic nitrogen oxide or organic boron oxide having hydroximic acid group (—C(=NOH)OH), hydroxamic acid group (—C(=O)NHOH), nitrolic acid group, nitrosolic acid group, nitronic acid group or the like, and salts thereof. These compounds may be used singly or as a mixture of two or more kinds.

Much more specifically mentioning the polymer gel molecules, the natural retention factor is preferably at least one kind selected from hyaluronic acids consisting of hyaluronic acid and its salts, amino acid, polyamino acid, pyrrolidonecarboxylic acid or its derivatives, urea or its derivatives, N-acetylglucosamine, animal and plant polysaccharides, coenzyme Q10, rice powder, gelatin, oligosaccharide, monosaccharides, saponins, plant peptide, phospholipid, sericin, chondroitin, ceramide, albumin, collagen, chitin, chitosan, and plant/seaweed extracts.

The average molecular weight of the hyaluronic acid or its salt among the above polymer gel molecules is desired to be in the range of 1,000 to 5,000,000, preferably 5,000 to 3,000,000. If the average molecular weight is less than 1,000, the effect of hyaluronic acid in exhibition of moisture retention function is low, so that such an average molecular weight is undesirable. If the average molecular weight exceeds 5,000,000, viscosity is so increased that an evil influence is sometimes exerted on the dispersibility of the particles, and as a result, it becomes difficult to uniformly bond the polymer gel molecules to the particle surfaces, so that such an average molecular weight is undesirable.

The "average molecular weight" referred to herein is an average molecular weight measured by a viscosity measuring method defined in the Japanese Pharmacopoeia General Test Methods.

The polymer gel molecules may be those of at least one compound selected from natural polymer compounds, itaconic acids and N-isopropylacrylamides, or at least one compound selected from copolymers of the above compounds and ester-based compounds or poly(meth)acrylic acid esters.

The natural polymer compound is preferably at least one compound selected from catechins, vitamins, tannins, polysaccharides, proteins, phospholipids, natural moisture retention factors, alginic acids, polyglutamic acids and polyaspartic acids, or its salt.

The catechins are preferably catechins derived from tea.

The vitamin is preferably at least one kind selected from vitamin, vitamin derivatives and vitamin-like substances having functions close to those of vitamin.

The tannin is preferably at least one kind selected from tannin, tannic acid, pyrogallol, gallic acid and gallic acid esters.

The plant/seaweed extract is preferably at least one kind selected from plant extracts, such as avocado extract, althea extract, arnica extract, angelica extract, aloe extract, almond oil, locust bean extract, rice plant extract, strawberry extract, fennel extract, turmeric extract, common mallow extract, asiasarum root extract, *perilla* extract, Japanese coptis extract, olive oil, white nettle extract, *hypericum* extract, *scutellaria* root extract, restharrow extract, *Artemisia capillaris* extract, chamomile extract, oat extract, glycyrrhiza extract, ivy extract, raspberry extract, Japanese honeysuckle extract, *Sasa Albo-marginata* extract, gardenia extract, grapefruit extract, *Sophora flavescens* extract, *sophora* root extract, watercress extract, black sugar extract, geranium herb extract, gentian extract, burdock extract, clematis vitalba leaf extract, wheat extract, wheat germ extract, sesame extract, comfrey extract, cactus extract, saponaria extract, crataegus fruit extract, salvia extract, ginger extract, *perilla* herb extract, *rehmmania* root extract, shear butter, *filipendula* extract, peony root extract, birch extract, Easter lily extract, cnidium rhizome extract, mallow extract, white mulberry extract, thyme extract, soybean extract, tea extracts, such as green tea, black tear and Oolong tea extracts, camellia extract, corn extract, Chinese caterpillar extract, tormentilla extract, Japanese angelica root extract, houttuynia extract, ophiopogon tuber extract, lupines extract, witch hazel extract, *mentha* herb extract, green *mentha* herb extract, peppermint extract, parsley extract, rose extract, sunflower extract, Japanese cypress extract, sponge gourd extract, grape extract, prune extract, butcher bloom extract, borage oil, paeonia extract, jojoba oil, linden extract, hop extract, pine extract, horse chestnut extract, *macadamia* nut oil, quince extract, *Swertia pseudochinensis* extract, meadowfoam extract balmmint extract, Mukurossi peel extract, Chinese quince extract, cornflower extract, lily extract, Yuzu extract, saxifrage extract, *coix* extract, *Siraitia grosvenorii* extract, lime extract, lavender extract, *Gentiana triflora* extract, burnet extract, apple extract and Chinese milk vetch extract; and seaweed extracts, e.g., brown algae, such as *Laminaria, Laminaria japonica, undaria pinnatifida, Hizikia fusiformis, Fucus distichus, Padina arborescens, Analipus japonicus, Nemacystis decipiens, Ishige okamurai, Endarachne binghamiae, Akkesiphycus lubricus, Colpomenia sinuosa, Myelophycus simplex, Hydroclathrus clathrates, Agarum cribrosum, Costaria costata, Kjellmaniella gyrata, Ecklonia cava, Ecklonia stolonifera, Alaria crassifolia, Pelvetia wrightii, Turbinaria ornate, Sargassum fulvellum, Sargassum ringgoldianum* and giant kelp; red algae, such as *Gelidiurn amansii, Beckerella subcostata, Gelidium japonicum, Pterocladia capillacea, Meristotheca papulosa, Encheuma denticulaturn, Chondrus ocellatus, Chondrus crispus, Gigartina tenella, Gigartina teedii, Grgartina intermedia, Enteromorpha linza, Bangia atropurpurea, Porphyra tenera, Scinaia japonica, Bonnemai-* sonia hamifera, Dudresnaya japonica, Grateloupia divaricata, Grateloupia filicina, Carpopeltis affinis, Pronitis crispate, Gloiopeltis, Hypnea charoides, Gracilaria verrucosa, Ceratodityon spongiosum, Palmaria pulmata, Ceramium kondoi, Campylaephora hypnaeoides, Congregatocarpus pasificus and Herposiphonia fissidentoides; and green algae, such as Chlorella, Enteromorpha, Dunaliella, Prochlorococcus, Ulva pertusa, Prasiola japonica, Cladophora aegagropila, Cladophora, Acetabularia ryukyuensis, Chaetomorpha spiralis, Chaetomorpha moniligera, Monostroma nitidum and Spirogyra.

The mean particle diameter of the organic-inorganic composite particles can be controlled by the amount of the polymer gel molecules to be bonded to the surfaces of the inorganic oxide particles and the time for swelling the polymer gel molecules, and this is one feature of the present invention.

The amount of the polymer gel molecules to be bonded to the surfaces of the inorganic oxide particles is desired to be in the range of 0.001 to 20% by weight, preferably 0.005 to 10% by weight, based on the total amount of the inorganic oxide particles. If the bonding amount is less than 0.001% by weight, it becomes difficult to exhibit functions of the polymer gel molecules (e.g., sensory property in the case where the organic-inorganic composite particles are used by adding them to cosmetics), so that such an amount is undesirable. If the bonding amount exceeds 20% by weight, interaction among the polymer gel molecules is strengthened to sometimes cause lowering of the functions of the polymer gel molecules, so that such an amount is undesirable.

The mean particle diameter of the organic-inorganic composite particles obtained as above is desired to be in the range of 0.1 to 300 μm, preferably 0.15 to 280 μm. Although organic-inorganic composite particles having a mean particle diameter of less than 0.1 μm can be also used, the scattering force of the particles is increased to make handling of the particles difficult, so that such particles are undesirable. If the mean particle diameter exceeds 300 μm, the spontaneous sedimentation force is increased to make it difficult to homogeneously disperse the particles in a solvent, similarly to the case of the aforesaid inorganic oxide particles, so that the upper limit is determined to be 300 μm.

The inorganic oxide particles may be those having been subjected to pulverization using a sample mill, a sand mill, a jet mill, a juicer mixer, a Yariya type crusher or the like to adjust their sizes to proper sizes.

As previously described, the organic-inorganic composite particles are used after they are dissolved in a solvent such as an aqueous solvent or a non-aqueous solvent.

As the solvent, a solvent capable of dissolving the polymer gel molecules can be used without any restriction. Examples of such solvents include water; alcohols, such as methanol, ethanol and isopropanol; ketones, such as acetone, ethyl methyl ketone and methyl isobutyl ketone; ethers, such as THF and dioxane; and amides, such as DMF and NMP. The solvent should be selected in consideration of the type of the polymer gel molecules, etc. These solvents may be used singly or as a mixture of two or more kinds. However, it is desirable to select the solvent from solvents which do not undergo phase separation from not only the solvents themselves but also the polymer gel molecules.

Further, the polymer gel molecules have water retention property by the mechanism that the polymer gel molecules incorporate or release water molecules by virtue of one or more hydroxyl groups present in a molecule, and by the change of an uptake of water molecules according to a change in the surrounding environment, molecular forms of the polymer gel molecules are changed and undergo shrinking or swelling. That is to say, swelling accompanies incorporation of water molecules, while shrinking means a phenomenon that the water molecules are released, as a reverse process to the swelling. Examples of the changes in the surrounding environment include: (1) changes of physical properties of a solvent (system) in which the polymer gel molecules are dispersed, such as changes of temperature and pH, and (2) changes accompanying a change of solvent composition, such as changes of dipole parameter, dielectric constant, viscosity and polarity, in the case of a mixed solvent system.

The swelling property is represented by a swell ratio and is defined by the following formula.

$$\text{Swell ratio} = \text{weight of polymer gel molecules after swelling/weight of polymer gel molecules before swelling} \quad (1)$$

In the measuring method, water is slowly dropwise added to 1 g of polymer gel molecules before swelling, then they are allowed to stand still for 18 hours, and when oozing of water (state where the polymer gel molecules are sufficiently swollen) is detected, the weight is measured, and the swell ratio is calculated from the formula (1). The polymer gel molecules for use in the present invention are preferably polymer gel molecules having a swell ratio of 10 to 8,000. For example, hyaluronic acid has a swell ratio of about 6,000.

It is preferable that the polymer gel molecules are in the molecule-swollen state in a solvent containing water as a main component, while they are in the molecule-shrunken state in a water-containing organic solvent containing an organic solvent as a main component.

Process for Producing Organic-Inorganic Composite Particles

The process for producing organic-inorganic composite particles of the present invention is a process for producing organic-inorganic composite particles comprising inorganic oxide particles each of which has a cationic charge on the particle surface and polymer gel molecules which are derived from a natural substance, have an anionic functional group and one or more hydroxyl groups in a molecule and have both of shrinking and swelling property, said polymer gel molecules being electrostatically bonded to surfaces of the inorganic oxide particles, said process comprising:

(1) a step wherein a solvent capable of shrinking the polymer gel molecules is added to a solution containing the polymer gel molecules and they are stirred, (2) a step wherein the inorganic oxide particles are added to the solution obtained in the step (1) and they are stirred to electrostatically bond the polymer gel molecules to the surfaces of the inorganic oxide particles, (3) a step wherein a solvent capable of swelling the polymer gel molecules is added to the dispersion obtained in the step (2) and they are stirred to swell the polymer gel molecules having been electrostatically bonded to the surfaces of the inorganic oxide particles, (4) a step wherein the dispersion obtained in the step (3) is filtered to separate a solid component, and (5) a step wherein the solid component obtained in the step (4) is dried.

Next, the steps of the production process are described below in detail.

Step (1)

In this step, to a solution obtained by dissolving the polymer gel molecules in a proper solvent at room temperature with stirring, a solvent for shrinking the polymer gel molecules is added with stirring, and they are further stirred at a rate of 200 to 700 rpm at room temperature for 1 to 4 hours. The solvent for dissolving the polymer gel molecules is selected from aqueous solvents and non-aqueous solvents capable of dissolving the polymer gel molecules. For dissolving the polymer gel molecules, the solvent can be heated if necessary, but preferable is a solvent capable of holding the polymer gel molecules in a dissolved state when it is cooled down to room temperature.

The solvent for shrinking the polymer gel molecules varies depending upon the type of the organic compound molecules, etc., and therefore, the solvent needs to be properly selected from aqueous solvents and non-aqueous solvents prior to use. As the solvent, a solvent which does not undergo phase separation from not only the solvent used for dissolving the polymer gel molecules but also the polymer gel molecules is preferably used.

Although the amount of the polymer gel molecules to be dissolved in the aqueous solvent or the non-aqueous solvent varies depending upon the type of the polymer gel molecules, the solubility thereof, etc., it is preferable to add the polymer gel molecules in such a proportion that the polymer gel molecules are contained in an amount of 0.5 to 3.0% by weight in the solvent.

Although the amount of the solvent for shrinking the polymer gel molecules varies depending upon the type of the solvent, the type of the polymer gel molecules, etc., it is preferable to add the solvent in such a proportion that the content of the polymer gel molecules in the resulting solution becomes 0.2 to 1.0% by weight. If the content of the polymer gel molecules is less than 0.2% by weight, the amount of the solvent used increases more than it is needed, so that such a content is undesirable. If the content of the polymer gel molecules exceeds 1.0% by weight, viscosity of the resulting solution is sometimes increased, so that such a content is undesirable.

Step (2)

In this step, to the polymer gel molecule-containing solution obtained in the step (1), the inorganic oxide particles are slowly added with stirring the solution, and they are further stirred at a rate of 200 to 700 rpm at room temperature for 1 to 6 hours.

Through the above operation, the polymer gel molecules are bonded to the surfaces of the inorganic oxide particles by means of electrostatic attraction. Although the stirring time varies depending upon the weight of the inorganic oxide particles added, etc., a period of time required for homogeneously dispersing the inorganic oxide particles in the dispersion is regarded as a measure. However, even if stirring is carried out for more than 6 hours, any particular effect is not obtained, so that stirring for more than 6 hours is not advisable.

Step (3)

In this step, a solvent for swelling the organic compound molecules is first added to the dispersion obtained in the step (2) with stirring the dispersion, and they are further stirred at a rate of 200 to 700 rpm at room temperature for 1 to 6 hours.

The solvent is added so that the content of the polymer gel molecules in the resulting solution may become 0.05 to 0.3% by weight. Although the stirring time varies depending upon the weight of the inorganic oxide particles (inorganic oxide particles to the surfaces of which the polymer gel molecules have been electrostatically bonded) contained in the solution, etc., a period of time required for homogeneously dispersing the inorganic oxide particles in the dispersion is regarded as a measure. However, even if stirring is carried out for more than 6 hours, any particular effect is not obtained, so that stirring for more than 6 hours is not advisable.

Subsequently, the stirring is terminated, and the dispersion is allowed to standstill for 6 to 24 hours at room temperature. Through this operation, the polymer gel molecules having been electrostatically bonded to the surfaces of the inorganic oxide particles are swollen. The time for allowing the dispersion to stand still varies depending upon the type of the polymer gel molecules, the bonding amount thereof, etc. If the time is less than 6 hours, there is a possibility that the polymer gel molecules cannot be completely swollen, so that such a time is undesirable. However, this does not apply to the case where the mean particle diameter of the particles needs to be controlled. Even if the dispersion is allowed to stand still for more than 24 hours, any particular effect is not obtained, so that allowing the dispersion to stand still for more than 24 hours is not advisable.

Step (4)

In the step (4), the organic-inorganic composite particle-containing solution obtained in the step (3) is filtered to separate a solid component.

Separation of the solid component composed of the organic-inorganic composite particles is carried out using a commercially available filtration device, such as Buchner funnel, filter press, horizontal belt filter, synchro-filter, pre-coat filter, drum filter, belt filter or tray filter. As the separation method, a conventional method is adoptable, but it is preferable to carry out the separation in a vacuum filtration system.

It is preferable to sufficiently wash the thus obtained cake-like substance of the organic-inorganic composite particles with the solvent added in the step (3).

Step (5)

Subsequently, the cake-like substance is preferably dried at normal pressure or under reduced pressure at a temperature of room temperature to 80° C., preferably room temperature to 60° C., over a period of 0.5 to 6 hours, preferably 1 to 3 hours. If the drying temperature is lower than room temperature, the cake-like substance cannot be sufficiently dried in a short period of time. If the drying temperature exceeds 80° C., the polymer gel molecules having been electrostatically bonded to the surfaces of the inorganic oxide particles are sometimes decomposed. Therefore, such temperatures are undesirable. In order to dry the cake-like substance of the organic-inorganic composite particles at a relatively low temperature in a short period of time, it is preferable to dry the cake-like substance in a vacuum drying system.

It is desirable that the thus obtained dry powder (particle group) of the organic-inorganic composite particles is set on a pulverization device or a crushing device, such as sample mill, jet mill, juicer mixer or Yariya type crusher, to crush aggregates or lumps in advance.

The process for producing organic-inorganic composite particles of the present invention is described hereinbefore, and an example of the process wherein hyaluronic acid is used as the polymer gel molecules is described below with reference to the above steps.

(1) Hyaluronic acid as the polymer gel molecules is dissolved in water that is a solvent, at room temperature with stirring. Subsequently, to this solution, acetone that is a solvent for shrinking the hyaluronic acid is added, and they are stirred at a rate of about 200 rpm at room temperature for about 2 hours, whereby the hyaluronic acid is shrunken in water.

(2) With stirring the hyaluronic acid-containing solution obtained in the step (1), inorganic oxide particles (e.g., alumina-coated silica particles) are slowly added to the solution, and they are further stirred at a rate of about 400 rpm at room temperature for about 3 hours, whereby the hyaluronic acid is bonded to the surfaces of the inorganic oxide particles by means of electrostatic attraction.

(3) With stirring the dispersion obtained in the step (2), water that is a solvent for swelling the hyaluronic acid is added to the dispersion, and they are further stirred at a rate of about 400 rpm at room temperature for about 3 hours. Then, the stirring is terminated, and the resulting dispersion is allowed to stand still for about 18 hours at room temperature, whereby the hyaluronic acid having been electrostatically bonded to the surfaces of the inorganic oxide particles are swollen.

(4) The solution containing organic-inorganic composite particles with hyaluronic acid, which is obtained in the step (3), is filtered to separate a solid component.

(5) The solid component (cake-like substance) obtained in the step (4) is dried at a temperature of about 60° C. over a period of about 3 hours.

Organic-Inorganic Composite Particle Dispersion

The organic-inorganic composite particle dispersion of the present invention is a dispersion obtained by dispersing the organic-inorganic composite particles in an amount of 0.001 to 50% by weight in a solvent selected from oils and fats, waxes, hydrocarbons, fatty acids, alcohols, alkyl glyceryl ethers, esters, polyhydric alcohols, saccharides, silicone oil, crosslinked silicone gel and fluorine oil, or a mixed solvent thereof.

As previously described, the organic-inorganic composite particles of the present invention have good dispersibility not only in aqueous solvents such as water but also in non-aqueous solvents, and besides, aggregation of the particles scarcely occurs, so that they can be easily dispersed in the above solvents. Even if the content of the organic-inorganic composite particles in the dispersion is less than 0.001% by weight, there is no specific problem, but the functions of the organic-inorganic composite particles cannot be exhibited depending upon their uses (e.g., cosmetics), so that such a content is undesirable. If the content of the organic-inorganic composite particles exceeds 50% by weight, viscosity of the solution is increased and aggregation of the particles sometimes occurs, so that such a content is undesirable.

Cosmetic

The cosmetic of the present invention is a cosmetic containing the organic-inorganic composite particles in an amount of 0.001 to 40% by weight.

The organic-inorganic composite particles are used by adding solids of the particles, as they are, to conventional cosmetic components, or by adding the organic-inorganic composite particle dispersion containing the particles to conventional cosmetic components. Even if the content of the organic-inorganic composite particles in the dispersion is less than 0.001% by weight, there is no specific problem, but the functions (e.g., sensory property) of the organic-inorganic composite particles cannot be exhibited depending upon their cosmetic uses, so that such a content is undesirable. If the content of the organic-inorganic composite particles exceeds 40% by weight, the functions of the organic-inorganic composite particles are excessively exhibited, or side effects (e.g., inflammation of skin) are sometimes brought about, so that such a content is undesirable.

Examples of the cosmetics include skin care cosmetics, base makeup cosmetics, cleansing cosmetics and body care cosmetics. Above all, the organic-inorganic composite particles of the present invention are preferably used for skin care cosmetics for moisture retention/prevention of skin irritation, acne, horny substance care, wrinkles/sags, dark skin/dark circle, ultraviolet light care, anti-oxidation care, etc.; base makeup cosmetics, such as powder foundation, liquid foundation, cream foundation, mousse foundation, pressed powder and makeup base; cleansing cosmetics, such as soap, cleansing foam and makeup removing cream; and body care cosmetics, such as those for cleansing, anti-suntan and prevention of hand chapping, and body powder.

Measuring Method and Evaluation Method

Measuring method and evaluation method used in the examples of the present invention, etc. are described below.

(1) Measuring Method for Mean Particle Diameter (a) Measuring Method A for Mean Particle Diameter The inorganic oxide particles or the organic-inorganic composite particles are dispersed in pure water to prepare a slurry (solids concentration: 1.0% by weight), and the slurry is irradiated with ultrasonic waves for 5 minutes using an ultrasonic pulverizer (TA-5287 type ultrasonic disintegrator manufactured by Kaijo Corporation) to well disperse the particles. Then, the resulting dispersion is set on a centrifugal sedimentation type particle size distribution measuring analyzer (CAPA-700 manufactured by Horiba Ltd.) to measure a particle size distribution of the particles, and a value of a particle diameter given when the cumulative size distribution based on the volume becomes 50% is taken as a mean particle diameter (so-called median diameter). By the way, in this measuring method, a mean particle diameter of a particle group having particle diameters of 0.01 to 300 μm dispersed in an aqueous solvent (pure water) can be measured.

(b) Measuring Method B for Mean Particle Diameter

The inorganic oxide particles or the organic-inorganic composite particles are dispersed in isononyl isononanoate (Salacos 99 (registered trademark) available from The Nisshin Oillio Group, Ltd.) to prepare a slurry (solids concentration: 1.0% by weight), and the slurry is irradiated with ultrasonic waves for 5 minutes using an ultrasonic pulverizer (TA-5287 type ultrasonic disintegrator manufactured by Kaijo Corporation) to well disperse the particles. Then, the resulting dispersion is set on a centrifugal sedimentation type particle size distribution measuring analyzer (CAPA-700 manufactured by Horiba Ltd.) to measure a particle size distribution of the particles, and a value of a particle diameter given when the cumulative size distribution based on the volume becomes 50% is taken as a mean particle diameter (so-called median diameter). By the way, in this measuring method, a mean particle diameter of a particle group having particle diameters of 0.01 to 300 μm dispersed in a non-aqueous solvent (isononyl isononoate) can be measured.

(2) Differential Thermal Measuring Method

About 30 mg of a powder of the organic-inorganic composite particles is placed in a platinum container, and it is set on a differential thermalgravimetric analyzer (differential thermalgravimetric Thermo plus TG8110 manufacture by Rigaku Corporation). With elevating the temperature from room temperature to 1000° C. at a rate of 10° C./min, the weight of the sample is measured in the atmosphere, and the amount of the polymer gel molecules (water content in the case of molecules having water absorption property) having been electrostatically bonded to the particle surfaces is determined from a weight change (%) of the sample.

(3) Evaluation Method for Dispersibility

Dispersibility of the organic-inorganic composite particles is evaluated by a mean particle diameter (so-called median diameter) of the organic-inorganic composite particles dispersed in isononyl isononanoate that is an organic solvent having poor affinity with water. The mean particle diameter is measured based on the above-mentioned mean particle diameter measuring method B. As the mean particle diameter (so-called median diameter) of the inorganic oxide particles after bonding of the polymer gel molecules is decreased as compared with the mean particle diameter (so-called median diameter) of the inorganic oxide particles before bonding of the polymer gel molecules, dispersibility of the organic-inorganic composite particles in the organic solvent is enhanced. The organic-inorganic composite particles having amphipathic property as above can be easily dispersed not only in a water solvent but also in an organic solvent having poor affinity with water, and aggregation of the particles does not occur in the organic solvent.

EXAMPLES

The present invention is further described with reference to the following examples, but it should be construed that the present invention is in no way limited to those examples. That is to say, examples in which hyaluronic acid or sericin is used as the polymer gel molecules derived from a natural substance are only shown below, but other substances can be used without any restriction as long as they have an anionic functional group and one or more hydroxyl groups in a molecule and have both of shrinking and swelling property. Moreover, a method for completely modifying surfaces of the inorganic oxide particles with the polymer gel molecules on the basis of "change in solution composition" that is one of change factors in the surrounding environment is described below, but other methods (e.g., change in temperature and change in pH) may be adopted.

Example 1

Preparation of Inorganic Oxide Particles (I) Having Cationic Surface Charge

In a 3-liter titanium tank, 68 g of silica particles (SILICA MICROBEADS (registered trademark) P-1500 available from JGC Catalysts and Chemicals Ltd., mean particle diameter measured by the measuring method A: 8.40 μm, mean particle diameter measured by the measuring method B: 26.37 μm) were placed, and 670 g of pure water was added so that the content of the solid component might become about 9% by weight. Next, a pH meter and a temperature sensor were installed in the titanium tank, and stirring was carried out at a rotational speed of 350 rpm for 2 hours using a titanium flat blade to obtain a slurry of the silica particles.

Next, the resulting slurry was heated up to a temperature of 70° C., and then, with stirring the slurry, a hydrochloric acid aqueous solution having a concentration of 10% was added to the slurry to adjust pH of the slurry to 6.00. With maintaining pH of the slurry at 6.00, 27 g of a highly basic aluminum chloride aqueous solution (PAC#1000 available from Taki Chemical Co., Ltd.) of about 5% by weight in terms of $Al_2O_3$ was added to the slurry over a period of 2 hours. Thereafter, the slurry was allowed to stand for 7 hours with stirring and with maintaining the temperature of the slurry at 70° C., whereby the surfaces of the silica particles were coated with an alumina component.

Subsequently, the temperature of the slurry was lowered down to room temperature, and then the slurry was filtrated with a Buchner funnel in vacuo. The slurry was washed with pure water of 1400 g that is 20 times the weight of the silica. Next, the resulting cake-like substance was dried at a temperature of 110° C. for 18 hours. Then, in order to disintegrate aggregates of the particles having been formed during drying, the dried substance was crushed by a sample mill to obtain 69 g of a dry powder of silica particles coated with alumina (referred to as "alumina-coated silica particles (I)" hereinafter). The mean particle diameter of the thus obtained alumina-coated silica particles (I), as measured by the aforesaid measuring method A, was 8.60 μm, and the mean particle diameter thereof, as measured by the aforesaid measuring method B, was 23.17 μm.

Preparation of Organic-Inorganic Composite Particles (A)

In a 300 ml glass beaker having a magnetic stirrer therein, 0.0012 g of hyaluronic acid (Hyaluronsan HA-LQ available from Kewpie Corporation, average molecular weight: 850,000 to 1,600,000) was placed, and 12 g of pure water was added so that the content of hyaluronic acid might become about 0.01% by weight. Then, they were stirred for 4 hours at room temperature to dissolve the hyaluronic acid in pure water. Subsequently, with stirring the solution, acetone which was a solvent for bringing about molecular shrinkage of hyaluronic acid was added to the solution so that the content of hyaluronic acid might become about 0.003% by weight, and they were further stirred for 2 hours at room temperature. The amount of acetone added was 36 g.

Next, to the solution (containing hyaluronic acid in the shrunken state) obtained as above, 12 g of the alumina-coated silica particles (I) prepared above were slowly added with stirring the solution, and they were further stirred for 2 hours at room temperature, whereby the hyaluronic acid was electrostatically bonded to the surfaces of the alumina-coated silica particles (I).

Subsequently, to this solution, 60 g of pure water for swelling the hyaluronic acid having been electrostatically bonded to the surfaces of the alumina-coated silica particles (I) was added with stirring the solution, and they were further stirred for 2 hours at room temperature. Thereafter, the stirring was terminated, and the solution was allowed to stand still for 18 hours at room temperature.

Next, the solid component contained in the standing liquid obtained as above was filtrated with a Buchner funnel in vacuo to obtain a cake-like substance. The cake-like substance was washed with 240 g (about 20 times the weight of the alumina-coated silica particles) of pure water.

Subsequently, the resulting cake-like substance was placed in a dryer maintained at a temperature of 60° C., dried for 4 hours and then subjected to vacuum drying in a desiccator maintained at room temperature. In order to disintegrate aggregates of the particles having been formed during drying, the dried substance was placed in a sample mill and crushed, whereby 11.88 g of a dry powder of alumina-coated silica particles to the surfaces of which hyaluronic acid had been electrostatically bonded (referred to as "organic-inorganic composite particles (A)" hereinafter) was obtained.

Dispersibility of the thus obtained organic-inorganic composite particles (A) was evaluated by the aforesaid dispersibility evaluation method, and as a result, it was 8.53 μm.

Subsequently, the organic-inorganic composite particles (A) were subjected to the aforesaid differential thermal analysis method (TG-DTA method), and as a result, a peak of a large amount of a water component, which was not detected from the surface of the base material (alumina-coated silica particles), was observed on the surfaces (areas where hyaluronic acid had been bonded) of the organic-inorganic composite particles. Moreover, a thermogravimetric change derived from hyaluronic acid was detected at around 400° C. though it was weak.

Example 2

Preparation of Organic-Inorganic Composite Particles (B)

In a 300 ml glass beaker having a magnetic stirrer therein, 0.0048 g of hyaluronic acid (Hyaluronsan HA-LQ available from Kewpie Corporation, average molecular weight: 850,000 to 1,600,000) was placed, and 48 g of pure water was added so that the content of hyaluronic acid might become about 0.01% by weight. Then, they were stirred for 4 hours at room temperature to dissolve the hyaluronic acid in pure water. Subsequently, with stirring the solution, acetone which was a solvent for bringing about molecular shrinkage of hyaluronic acid was added to the solution so that the content (concentration) of hyaluronic acid might become about 0.003% by weight, and they were further stirred at room temperature. The amount of acetone added was 144 g.

Next, to the solution (containing hyaluronic acid in the shrunken state) obtained as above, 12 g of the alumina-coated silica particles (I) prepared above were slowly added with stirring the solution, and they were further stirred for 2 hours at room temperature, whereby the hyaluronic acid was electrostatically bonded to the surfaces of the alumina-coated silica particles (I).

Next, to this solution, 60 g of pure water for swelling the hyaluronic acid having been electrostatically bonded to the surfaces of the alumina-coated silica particles (I) was added with stirring the solution, and they were further stirred for 2 hours at room temperature. Thereafter, the stirring was terminated, and the solution was allowed to stand still for 18 hours at room temperature.

Subsequently, the solid component contained in the standing liquid obtained as above was filtrated with a Buchner funnel in vacuo to obtain a cake-like substance. The cake-like substance was washed with 240 g (about 20 times the weight of the alumina-coated silica particles (I)) of pure water.

Subsequently, the resulting cake-like substance was placed in a dryer maintained at a temperature of 60° C., dried for 4 hours and then subjected to vacuum drying in a desiccator maintained at room temperature. In order to disintegrate aggregates of the particles having been formed during drying, the dried substance was placed in a sample mill and crushed, whereby 11.96 g of a dry powder of alumina-coated silica particles to the surfaces of which hyaluronic acid had been electrostatically bonded (referred to as "organic-inorganic composite particles (B)" hereinafter) was obtained.

Dispersibility of the thus obtained organic-inorganic composite particles (B) was evaluated by the aforesaid dispersibility evaluation method, and as a result, it was 8.59 μm.

Subsequently, the organic-inorganic composite particles (B) were subjected to the aforesaid differential thermal method (TG-DTA method), and as a result, a peak of a large amount of a water component, which was not detected from the surface of the base material (alumina-coated silica particles), was observed on the surfaces (areas where hyaluronic acid had been bonded) of the organic-inorganic composite particles. Moreover, a thermogravimetric change derived from hyaluronic acid was detected at around 400° C. though it was weak.

Example 3

Preparation of Inorganic Oxide Particles (II) Having Cationic Surface Charge

In a 3-liter titanium tank, 68 g of silica particles (SILICA MICROBEADS (registered trademark) P-1500 available from JGC Catalysts and Chemicals Ltd., mean particle diameter measured by the measuring method A: 8.40 μm, mean particle diameter measured by the measuring method B: 26.37 μm) were placed, and 670 g of pure water was added so that the content of the solid component might become about 9% by weight. Next, a pH meter and a temperature sensor were installed in the titanium tank, and stirring was carried out at a rotational speed of 350 rpm for 2 hours using a titanium flat blade to obtain a slurry of the silica particles.

Next, the resulting slurry was heated up to a temperature of 70° C., and then, with stirring the slurry, a hydrochloric acid aqueous solution having a concentration of 10% was added to the slurry to adjust pH of the slurry to 6.00. With maintaining pH of the slurry at 6.00, 11 g of a highly basic aluminum chloride aqueous solution (PAC#1000 available from Taki Chemical Co., Ltd.) of about 2% by weight in terms of $Al_2O_3$ was added to the slurry over a period of 2 hours. Thereafter, the slurry was allowed to stand for 7 hours with stirring and with maintaining the temperature of the slurry at 70° C., whereby the surfaces of the silica particles were coated with an alumina component.

Subsequently, the temperature of the slurry was lowered down to room temperature, and then the slurry was filtrated with a Buchner funnel in vacuo. The slurry was washed with pure water of 1400 g that is 20 times the weight of the silica. Next, the resulting cake-like substance was dried at a temperature of 110° C. for 18 hours. Then, in order to disintegrate aggregates of the particles having been formed during drying, the dried substance was crushed by a sample mill to obtain 69 g of a dry powder of silica particles coated with alumina (referred to as "alumina-coated silica particles (II)" hereinafter). The mean particle diameter of the thus obtained alumina-coated silica particles (II), as measured by the aforesaid measuring method A, was 10.42 μm, and the mean particle diameter thereof, as measured by the aforesaid measuring method B, was 26.37 μm.

Preparation of Organic-Inorganic Composite Particles (C)

In a 500 ml glass beaker having a magnetic stirrer therein, 0.120 g of hyaluronic acid (Hyaluronsan HA-LQ available from Kewpie Corporation, average molecular weight: 850,000 to 1,600,000) was placed, and 12 g of pure water was added so that the content of hyaluronic acid might become about 1% by weight. Then, they were stirred for 4 hours at room temperature to dissolve the hyaluronic acid in pure water. Subsequently, with stirring the solution, acetone which was a solvent for bringing about molecular shrinkage of hyaluronic acid was added to the solution so that the content of hyaluronic acid might become about 0.3% by weight, and they were further stirred for 2 hours at room temperature. The amount of acetone added was 35 g.

Next, to the solution (containing hyaluronic acid in the shrunken state) obtained as above, 12 g of the alumina-coated silica particles (II) prepared above were slowly added with stirring the solution, and they were further stirred for 2 hours at room temperature, whereby the hyaluronic acid was electrostatically bonded to the surfaces of the alumina-coated silica particles (II).

Subsequently, to this solution, 60 g of pure water for swelling the hyaluronic acid having been electrostatically bonded to the surfaces of the alumina-coated silica particles (II) was added with stirring the solution, and they were further stirred for 2 hours at room temperature. Thereafter, the stirring was terminated, and the solution was allowed to stand still for 18 hours at room temperature.

Next, the solid component contained in the standing liquid obtained as above was filtrated with a Buchner funnel in vacuo to obtain a cake-like substance. The cake-like substance was washed with 240 g (about 20 times the weight of the alumina-coated silica particles (II)) of pure water.

Subsequently, the resulting cake-like substance was placed in a dryer maintained at a temperature of 60° C., dried for 4 hours and then subjected to vacuum drying in a desiccator maintained at room temperature. In order to disintegrate aggregates of the particles having been formed during drying, the dried substance was placed in a sample mill and crushed, whereby 12.26 g of a dry powder of alumina-coated silica particles to the surfaces of which hyaluronic acid had been electrostatically bonded (referred to as "organic-inorganic composite particles (C)" hereinafter) was obtained.

Dispersibility of the thus obtained organic-inorganic composite particles (C) was evaluated by the aforesaid dispersibility evaluation method, and as a result, it was 11.23 μm.

Subsequently, the organic-inorganic composite particles (C) were subjected to the aforesaid differential thermal method (TG-DTA method), and as a result, a peak of a large amount of a water component, which was not detected from the surface of the base material (alumina-coated silica particles), was observed on the surfaces (areas where hyaluronic acid had been bonded) of the organic-inorganic composite particles. Moreover, a thermogravimetric change derived from hyaluronic acid was detected at around 400° C. though it was weak.

Example 4

Preparation of Organic-Inorganic Composite Particles (D)

In a 500 ml glass beaker having a magnetic stirrer therein, 0.480 g of hyaluronic acid (Hyaluronsan HA-LQ available from Kewpie Corporation, average molecular weight: 850,000 to 1,600,000) was placed, and 48 g of pure water was added so that the content of hyaluronic acid might become about 1% by weight. Then, they were stirred for 4 hours at room temperature to dissolve the hyaluronic acid in pure water. Subsequently, with stirring the solution, acetone which was a solvent for bringing about molecular shrinkage of hyaluronic acid was added to the solution so that the content of hyaluronic acid might become about 0.3% by weight, and they were further stirred for 2 hours at room temperature. The amount of acetone added was 145 g.

Next, to the solution (containing hyaluronic acid in the shrunken state) obtained as above, 12 g of the alumina-coated silica particles (II) prepared above were slowly added with stirring the solution, and they were further stirred for 2 hours at room temperature, whereby the hyaluronic acid was electrostatically bonded to the surfaces of the alumina-coated silica particles (II).

Subsequently, to this solution, 204 g of pure water for swelling the hyaluronic acid having been electrostatically bonded to the surfaces of the alumina-coated silica particles (II) was added with stirring the solution, and they were further stirred for 2 hours at room temperature. Thereafter, the stirring was terminated, and the solution was allowed to stand still for 18 hours at room temperature.

Next, the solid component contained in the standing liquid obtained as above was filtrated with a Buchner funnel in vacuo to obtain a cake-like substance. The cake-like substance was washed with 240 g (about 20 times the weight of the alumina-coated silica particles (II)) of pure water.

Subsequently, the resulting cake-like substance was placed in a dryer maintained at a temperature of 60° C., dried for 4 hours and then subjected to vacuum drying in a desiccator maintained at room temperature. In order to disintegrate aggregates of the particles having been formed during drying, the dried substance was placed in a sample mill and crushed, whereby 12.51 g of a dry powder of alumina-coated silica particles to the surfaces of which hyaluronic acid had been electrostatically bonded (referred to as "organic-inorganic composite particles (D)" hereinafter) was obtained.

Dispersibility of the thus obtained organic-inorganic composite particles (D) was evaluated by the aforesaid dispersibility evaluation method, and as a result, it was 10.33 μm.

Subsequently, the organic-inorganic composite particles (D) were subjected to the aforesaid differential thermal method (TG-DTA method), and as a result, a peak of a large amount of a water component, which was not detected from the surface of the base material (alumina-coated silica particles), was observed on the surfaces (areas where hyaluronic acid had been bonded) of the organic-inorganic composite particles. Moreover, a thermogravimetric change derived from hyaluronic acid was detected at around 400° C. though it was weak.

Example 5

Preparation of Organic-Inorganic Composite Particles (E)

In a 500 ml glass beaker having a magnetic stirrer therein, 0.480 g of hyaluronic acid (Sodium Biohyaluronate available from Shiseido Co., Ltd., average molecular weight: 1,100,000 to 1,600,000) was placed, and 48 g of pure water was added so that the content of hyaluronic acid might become about 1% by weight. Then, they were stirred for 4 hours at room temperature to dissolve the hyaluronic acid in pure water. Subsequently, with stirring the solution, acetone which was a solvent for bringing about molecular shrinkage of hyaluronic acid was added to the solution so that the content of hyaluronic acid might become about 0.3% by weight, and they were further stirred for 2 hours at room temperature. The amount of acetone added was 144 g.

Next, to the solution (containing hyaluronic acid in the shrunken state) obtained as above, 12 g of the alumina-coated silica particles (II) prepared above were added with stirring the solution, and they were further stirred for 2 hours at room temperature, whereby the hyaluronic acid was electrostatically bonded to the surfaces of the alumina-coated silica particles (II).

Subsequently, to this solution, 205 g of pure water for swelling the hyaluronic acid having been electrostatically bonded to the surfaces of the alumina-coated silica particles (II) was added with stirring the solution, and they were further stirred for 2 hours at room temperature. Thereafter, the stirring was terminated, and the solution was allowed to stand still for 18 hours at room temperature.

Next, the solid component contained in the standing liquid obtained as above was filtrated with a Buchner funnel in vacuo to obtain a cake-like substance. The cake-like substance was washed with 240 g (about 20 times the weight of the alumina-coated silica particles (II)) of pure water.

Subsequently, the resulting cake-like substance was placed in a dryer maintained at a temperature of 60° C., dried for 4 hours and then subjected to vacuum drying in a desiccator maintained at room temperature. In order to disintegrate aggregates of the particles having been formed during drying, the dried substance was placed in a sample mill and crushed, whereby 12.51 g of a dry powder of alumina-coated silica particles to the surfaces of which hyaluronic acid had been electrostatically bonded (referred to as "organic-inorganic composite particles (E)" hereinafter) was obtained.

Dispersibility of the thus obtained organic-inorganic composite particles (E) was evaluated by the aforesaid dispersibility evaluation method, and as a result, it was 10.50 µm.

Subsequently, the organic-inorganic composite particles (E) were subjected to the aforesaid differential thermal method (TG-DTA method), and as a result, a peak of a large amount of a water component, which was not detected from the base material, was observed on the surfaces (areas where hyaluronic acid had been bonded) of the organic-inorganic composite particles. Moreover, a thermogravimetric change derived from hyaluronic acid was detected at around 400° C. though it was weak.

Example 6

Preparation of Inorganic Oxide Particles (III) Having Cationic Surface Charge

In a 5-liter titanium tank, 53 g of silica particles (SILICA MICROBEADS (registered trademark) P-1500 available from JGC Catalysts and Chemicals Ltd., mean particle diameter measured by the measuring method A: 8.40 µm, mean particle diameter measured by the measuring method B: 26.37 µm) were placed, and 470 g of pure water was added so that the content of the solid component might become about 9% by weight. Next, a pH meter and a temperature sensor were installed in the titanium tank, and stirring was carried out at a rotational speed of 200 rpm for 2 hours using a titanium flat blade to obtain a slurry of the silica particles.

Next, the resulting slurry was heated up to a temperature of 70° C., and then, with stirring the slurry, an ammonia aqueous solution having a concentration of 15% was added to the slurry to adjust pH of the slurry to 9.35. With maintaining pH of the slurry at 9.35, 5 g of magnesium chloride (available from Kanto Chemical Co., Ltd.) of about 10% by weight in terms of MgO was added to the slurry over a period of 6 hours. Thereafter, the slurry was allowed to stand for 13 hours with stirring and with maintaining the temperature of the slurry at 70° C., whereby the surfaces of the silica particles were coated with a magnesium oxide component.

Subsequently, the temperature of the slurry was lowered down to room temperature, and then the slurry was filtrated with a Buchner funnel in vacuo. The slurry was washed with pure water of 1100 g that is 20 times the weight of the silica. Next, the resulting cake-like substance was dried at a temperature of 110° C. for 18 hours. Then, in order to disintegrate aggregates of the particles having been formed during drying, the dried substance was crushed by a sample mill to obtain 53 g of a dry powder of silica particles coated with magnesium oxide (referred to as "magnesium oxide-coated silica particles (III)" hereinafter). The mean particle diameter of the thus obtained magnesium oxide-coated silica particles (III), as measured by the aforesaid measuring method A, was 8.26 µm, and the mean particle diameter thereof, as measured by the aforesaid measuring method B, was 28.67 µm.

Preparation of Organic-Inorganic Composite Particles (F)

In a 300 ml glass beaker having a magnetic stirrer therein, 0.120 g of hyaluronic acid (Hyaluronsan HA-LQ available from Kewpie Corporation, average molecular weight: 850,000 to 1,600,000) was placed, and 12 g of pure water was added so that the content of hyaluronic acid might become about 1% by weight. Then, they were stirred for 4 hours at room temperature to dissolve the hyaluronic acid in pure water. Subsequently, with stirring the solution, acetone which was a solvent for bringing about molecular shrinkage of hyaluronic acid was added to the solution so that the content of hyaluronic acid might become about 0.3% by weight, and they were further stirred for 2 hours at room temperature. The amount of acetone added was 36 g.

Next, to the solution (containing hyaluronic acid in the shrunken state) obtained as above, 12 g of the magnesium oxide-coated silica particles (III) prepared above were slowly added with stirring the solution, and they were further stirred for 2 hours at room temperature, whereby the hyaluronic acid was electrostatically bonded to the surfaces of the magnesium oxide-coated silica particles (III).

Subsequently, to this solution, 60 g of pure water for swelling the hyaluronic acid having been electrostatically bonded to the surfaces of the magnesium oxide-coated silica particles (III) was added with stirring the solution, and they were further stirred for 2 hours at room temperature. Thereafter, the stirring was terminated, and the solution was allowed to stand still for 18 hours at room temperature.

Next, the solid component contained in the standing liquid obtained as above was filtrated with a Buchner funnel in vacuo to obtain a cake-like substance. The cake-like substance was washed with 240 g (about 20 times the weight of the magnesium oxide-coated silica particles (III)) of pure water.

Subsequently, the resulting cake-like substance was placed in a dryer maintained at a temperature of 60° C., dried for 4 hours and then subjected to vacuum drying in a desiccator maintained at room temperature. In order to disintegrate aggregates of the particles having been formed during drying, the dried substance was placed in a sample mill and crushed, whereby 12.26 g of a dry powder of magnesium oxide-coated silica particles to the surfaces of which hyaluronic acid had been electrostatically bonded (referred to as "organic-inorganic composite particles (F)" hereinafter) was obtained.

Dispersibility of the thus obtained organic-inorganic composite particles (F) was evaluated by the aforesaid dispersibility evaluation method, and as a result, it was 9.38 µm.

Subsequently, the organic-inorganic composite particles (F) were subjected to the aforesaid differential thermal method (TG-DTA method), and as a result, a peak of a large amount of a water component, which was not detected from the surface of the base material (magnesium oxide-coated silica particles (III)), was observed on the surfaces (areas where hyaluronic acid had been bonded) of the organic-inorganic composite particles. Moreover, a thermogravimetric change derived from hyaluronic acid was detected at around 400° C. though it was weak.

Example 7

Preparation of Organic-Inorganic Composite Particles (G)

In a 300 ml glass beaker having a magnetic stirrer therein, 0.480 g of hyaluronic acid (Hyaluronsan HA-LQ available from Kewpie Corporation, average molecular weight: 850,000 to 1,600,000) was placed, and 48 g of pure water was added so that the content of hyaluronic acid might become about 1% by weight. Then, they were stirred for 4 hours at room temperature to dissolve the hyaluronic acid in pure water. Subsequently, with stirring the solution, acetone which was a solvent for bringing about molecular shrinkage of hyaluronic acid was added to the solution so that the content of hyaluronic acid might become about 0.3% by weight, and they were further stirred for 2 hours at room temperature. The amount of acetone added was 144 g.

Next, to the solution (containing hyaluronic acid in the shrunken state) obtained as above, 12 g of the magnesium oxide-coated silica particles (III) prepared above were slowly added with stirring the solution, and they were further stirred for 2 hours at room temperature, whereby the hyaluronic acid was electrostatically bonded to the surfaces of the magnesium oxide-coated silica particles (III).

Subsequently, to this solution, 205 g of pure water for swelling the hyaluronic acid having been electrostatically bonded to the surfaces of the magnesium oxide-coated silica particles (III) was added with stirring the solution, and they were further stirred for 2 hours at room temperature. Thereafter, the stirring was terminated, and the solution was allowed to stand still for 18 hours at room temperature.

Next, the solid component contained in the standing liquid obtained as above was filtrated with a Buchner funnel in vacuo to obtain a cake-like substance. The cake-like substance was washed with 240 g (about 20 times the weight of the magnesium oxide-coated silica particles (III)) of pure water.

Subsequently, the resulting cake-like substance was placed in a dryer maintained at a temperature of 60° C., dried for 4 hours and then subjected to vacuum drying in a desiccator maintained at room temperature. In order to disintegrate aggregates of the particles having been formed during drying, the dried substance was placed in a sample mill and crushed, whereby 12.51 g of a dry powder of magnesium oxide-coated silica particles to the surfaces of which hyaluronic acid had been electrostatically bonded (referred to as "organic-inorganic composite particles (G)" hereinafter) was obtained.

Dispersibility of the thus obtained organic-inorganic composite particles (G) was evaluated by the aforesaid dispersibility evaluation method, and as a result, it was 9.42 µm.

Subsequently, the organic-inorganic composite particles (G) were subjected to the aforesaid differential thermal method (TG-DTA method), and as a result, a peak of a large amount of a water component, which was not detected from the surface of the base material (magnesium oxide-coated silica particles (III)), was observed on the surfaces (areas where hyaluronic acid had been bonded) of the organic-inorganic composite particles. Moreover, a thermogravimetric change derived from hyaluronic acid was detected at around 400° C. though it was weak.

Example 8

Preparation of Organic-Inorganic Composite Particles (H)

In a 500 ml glass beaker having a magnetic stirrer therein, 0.480 g of hyaluronic acid (Sodium Biohyaluronate available from Shiseido Co., Ltd., average molecular weight: 1,100,000 to 1,600,000) was placed, and 48 g of pure water was added so that the content of hyaluronic acid might become about 1% by weight. Then, they were stirred for 4 hours at room temperature to dissolve the hyaluronic acid in pure water. Subsequently, with stirring the solution, acetone which was a solvent for bringing about molecular shrinkage of hyaluronic acid was added to the solution so that the content of hyaluronic acid might become about 0.3% by weight, and they were further stirred for 2 hours at room temperature. The amount of acetone added was 144 g.

Next, to the solution (containing hyaluronic acid in the shrunken state) obtained as above, 12 g of the magnesium oxide-coated silica particles (III) prepared above were slowly added with stirring the solution, and they were further stirred for 2 hours at room temperature, whereby the hyaluronic acid was electrostatically bonded to the surfaces of the magnesium oxide-coated silica particles (III).

Subsequently, to this solution, 205 g of pure water for swelling the hyaluronic acid having been electrostatically bonded to the surfaces of the magnesium oxide-coated silica particles (III) was added with stirring the solution, and they were further stirred for 2 hours at room temperature. Thereafter, the stirring was terminated, and the solution was allowed to stand still for 18 hours at room temperature.

Next, the solid component contained in the standing liquid obtained as above was filtrated with a Buchner funnel in vacuo to obtain a cake-like substance. The cake-like substance was washed with 240 g (about 20 times the weight of the magnesium oxide-coated silica particles (III)) of pure water.

Subsequently, the resulting cake-like substance was placed in a dryer maintained at a temperature of 60° C., dried for 4 hours and then subjected to vacuum drying in a desiccator maintained at room temperature. In order to disintegrate aggregates of the particles having been formed during drying, the dried substance was placed in a sample mill and crushed, whereby 12.51 g of a dry powder of magnesium oxide-coated silica particles to the surfaces of which hyaluronic acid had been electrostatically bonded (referred to as "organic-inorganic composite particles (H)" hereinafter) was obtained.

Dispersibility of the thus obtained organic-inorganic composite particles (H) was evaluated by the aforesaid dispersibility evaluation method, and as a result, it was 9.58 µm.

Subsequently, the organic-inorganic composite particles (H) were subjected to the aforesaid differential thermal method (TG-DTA method), and as a result, a peak of a large amount of a water component, which was not detected from the surface of the base material (magnesium oxide-coated silica particles), was observed on the surfaces (areas where hyaluronic acid had been bonded) of the organic-inorganic composite particles. Moreover, a thermogravimetric change derived from hyaluronic acid was detected at around 400° C. though it was weak.

Example 9

Preparation of Organic-Inorganic Composite Particles (I)

In a 300 ml glass beaker having a magnetic stirrer therein, 0.20 g of hyaluronic acid (Hyalo-Oligo (registered trademark) available from Kewpie Corporation, average molecular weight: not more than 10,000) was placed, and 20 g of pure water was added so that the content of hyaluronic acid might become about 1% by weight. Then, they were stirred for 4 hours at room temperature to dissolve the hyaluronic acid in pure water. Subsequently, with stirring the solution, acetone which was a solvent for bringing about molecular shrinkage of hyaluronic acid was added to the solution so that the content of hyaluronic acid might become about 0.3% by weight, and they were further stirred for 2 hours at room temperature. The amount of acetone added was 60 g.

Next, to the solution (containing hyaluronic acid in the shrunken state) obtained as above, 5 g of the magnesium oxide-coated silica particles (III) prepared above were slowly added with stirring the solution, and they were further stirred for 2 hours at room temperature, whereby the hyaluronic acid was electrostatically bonded to the surfaces of the magnesium oxide-coated silica particles (III).

Subsequently, to this solution, 80 g of pure water for swelling the hyaluronic acid having been electrostatically bonded to the surfaces of the magnesium oxide-coated silica particles (III) was added with stirring the solution, and they were further stirred for 2 hours at room temperature. Thereafter, the stirring was terminated, and the solution was allowed to stand still for 18 hours at room temperature.

Next, the solid component contained in the standing liquid obtained as above was filtrated with a Buchner funnel in vacuo to obtain a cake-like substance. The cake-like substance (hyaluronic acid-bonded magnesium oxide-coated silica particles) was washed with 100 g (about 20 times the weight of the magnesium oxide-coated silica particles) of pure water.

Moreover, in a 1 liter glass beaker having a magnetic stirrer therein, 0.20 g of hyaluronic acid (Hyaluronsan HA-LQ available from Kewpie Corporation, average molecular weight: 850,000 to 1,600,000) was placed, and 20 g of pure water was added so that the content of hyaluronic acid might become about 1% by weight. Then, they were stirred for 4 hours at room temperature to dissolve the hyaluronic acid in pure water. Subsequently, with stirring the solution, acetone which was a solvent for bringing about molecular shrinkage of hyaluronic acid was added to the solution so that the content of hyaluronic acid might become about 0.3% by weight, and they were further stirred for 2 hours at room temperature. The amount of acetone added was 60 g.

Next, to the solution (containing hyaluronic acid in the shrunken state) obtained as above, 5 g of the hyaluronic acid-bonded magnesium oxide-coated silica particles prepared above were slowly added with stirring the solution, and they were further stirred for 2 hours at room temperature, whereby the hyaluronic acid was electrostatically bonded to the surfaces of the hyaluronic acid-bonded magnesium oxide-coated silica particles.

Subsequently, to this solution, 80 g of pure water for swelling the hyaluronic acid having been electrostatically bonded to the surfaces of the hyaluronic acid-bonded magnesium oxide-coated silica particles was added with stirring the solution, and they were further stirred for 2 hours at room temperature. Thereafter, the stirring was terminated, and the solution was allowed to stand still for 18 hours at room temperature.

Next, the solid component contained in the standing liquid obtained as above was filtrated with a Buchner funnel in vacuo to obtain a cake-like substance. The cake-like substance was washed with 100 g (about 20 times the weight of the hyaluronic acid-bonded magnesium oxide-coated silica particles) of pure water.

Subsequently, the resulting cake-like substance was placed in a dryer maintained at a temperature of 60° C., dried for 4 hours and then subjected to vacuum drying in a desiccator maintained at room temperature. In order to disintegrate aggregates of the particles having been formed during drying, the dried substance was placed in a sample mill and crushed, whereby 5.11 g of a dry powder of magnesium oxide-coated silica particles to the surfaces of which hyaluronic acid had been electrostatically bonded (referred to as "organic-inorganic composite particles (I)" hereinafter) was obtained.

Dispersibility of the thus obtained organic-inorganic composite particles (I) was evaluated, and as a result, it was 9.59 µm.

Subsequently, the organic-inorganic composite particles (I) were subjected to the aforesaid differential thermobalance method (TG-DTA method), and as a result, a peak of a large amount of a water component, which was not detected from the surface of the base material (magnesium oxide-coated silica particles), was observed on the surfaces (areas where hyaluronic acid had been bonded) of the organic-inorganic composite particles. Moreover, a thermogravimetric change derived from hyaluronic acid was detected at around 400° C. though it was weak.

Example 10

Preparation of Organic-Inorganic Composite Particles (J)

In a 500 ml glass beaker having a magnetic stirrer therein, 0.120 g of hyaluronic acid (Hyaluronsan HA-LQ available from Kewpie Corporation, average molecular weight: 850,000 to 1,600,000) was placed, and 12 g of pure water was added so that the content of hyaluronic acid might become about 1% by weight. Then, they were stirred for 4 hours at room temperature to dissolve the hyaluronic acid in pure water. Subsequently, with stirring the solution, acetone which was a solvent for bringing about molecular shrinkage of hyaluronic acid was added to the solution so that the content of hyaluronic acid might become about 0.3% by weight, and they were further stirred for 2 hours at room temperature. The amount of acetone added was 35 g.

Next, to the solution (containing hyaluronic acid in the shrunken state) obtained as above, 12 g of the alumina-coated silica particles (II) prepared above were slowly added with stirring the solution, and they were further stirred for 2 hours at room temperature, whereby the hyaluronic acid was electrostatically bonded to the surfaces of the alumina-coated silica particles (II).

Subsequently, the solid component contained in the slurry was filtrated with a Buchner funnel in vacuo to obtain a cake-like substance. The cake-like substance was washed with 240 g (about 20 times the weight of the alumina-coated silica particles (II)) of acetone.

Subsequently, the resulting cake-like substance was placed in a dryer maintained at a temperature of 60° C., dried for 4 hours and then subjected to vacuum drying in a desiccator maintained at room temperature. In order to disintegrate aggregates of the particles having been formed during drying, the dried substance was placed in a sample mill and crushed, whereby 12.18 g of a dry powder of alumina-coated silica particles to the surfaces of which hyaluronic acid had been electrostatically bonded (referred to as "organic-inorganic composite particles (J)" hereinafter) was obtained.

Dispersibility of the thus obtained organic-inorganic composite particles (J) was evaluated, and as a result, it was 7.44 µm.

Subsequently, the organic-inorganic composite particles (J) were subjected to the aforesaid differential thermal method (TG-DTA method), and as a result, a peak of a large amount of a water component, which was not detected from the surface of the base material (alumina-coated silica particles), was observed on the surfaces (areas where hyaluronic acid had been bonded) of the organic-inorganic composite particles. Moreover, a thermogravimetric change derived from hyaluronic acid was detected at around 400° C. though it was weak.

Example 11

Preparation of Organic-Inorganic Composite Particles (K)

In a 500 ml glass beaker having a magnetic stirrer therein, 0.480 g of hyaluronic acid (Hyaluronsan HA-LQ available from Kewpie Corporation, average molecular weight: 850,000 to 1,600,000) was placed, and 48 g of pure water was added so that the content of hyaluronic acid might become about 1% by weight. Then, they were stirred for 4 hours at room temperature to dissolve the hyaluronic acid in pure water. Subsequently, with stirring the solution, acetone which was a solvent for bringing about molecular shrinkage of hyaluronic acid was added to the solution so that the content of hyaluronic acid might become about 0.3% by weight, and they were further stirred for 2 hours at room temperature. The amount of acetone added was 145 g.

Next, to the solution (containing hyaluronic acid in the shrunken state) obtained as above, 12 g of the alumina-coated silica particles (II) prepared above were slowly added with stirring the solution, and they were further stirred for 2 hours at room temperature, whereby the hyaluronic acid was electrostatically bonded to the surfaces of the alumina-coated silica particles (II).

Subsequently, the solid component contained in the slurry was filtrated with a Buchner funnel in vacuo to obtain a cake-like substance. The cake-like substance was washed with 240 g (about 20 times the weight of the alumina-coated silica particles (II)) of acetone.

Subsequently, the resulting cake-like substance was placed in a dryer maintained at a temperature of 60° C., dried for 4 hours and then subjected to vacuum drying in a desiccator maintained at room temperature. In order to disintegrate aggregates of the particles having been formed during drying, the dried substance was placed in a sample mill and crushed, whereby 11.96 g of a dry powder of alumina-coated silica particles to the surfaces of which hyaluronic acid had been electrostatically bonded (referred to as "organic-inorganic composite particles (K)" hereinafter) was obtained.

Dispersibility of the thus obtained organic-inorganic composite particles (K) was evaluated, and as a result, it was 8.59 μm.

Subsequently, the organic-inorganic composite particles (K) were subjected to the aforesaid differential thermobalance method (TG-DTA method), and as a result, a peak of a large amount of a water component, which was not detected from the surface of the base material (alumina-coated silica particles), was observed on the surfaces (areas where hyaluronic acid had been bonded) of the organic-inorganic composite particles. Moreover, a thermogravimetric change derived from hyaluronic acid was detected at around 400° C. though it was weak.

Example 12

Preparation of Organic-Inorganic Composite Particles (L)

In a 300 ml glass beaker having a magnetic stirrer therein, 0.91 g of sericin (SILKGEN (registered trademark) G SOLUBLES-E available from Ichimaru Pharcos Co., Ltd., 5.5% by weight, average molecular weight: 5,500 to 40,000) was placed, and 4 g of ethanol was added so that the content of sericin might become about 1% by weight. Subsequently, with stirring the solution, acetone which was a solvent for bringing about molecular shrinkage of sericin was added to the solution so that the content of sericin might become about 0.3% by weight, and they were further stirred for 2 hours at room temperature. The amount of acetone added was 12 g.

Next, to the solution (containing sericin in the shrunken state) obtained as above, 5 g of the alumina-coated silica particles (II) prepared above were slowly added with stirring the solution, and they were further stirred for 2 hours at room temperature, whereby the sericin was electrostatically bonded to the surfaces of the alumina-coated silica particles (II).

Subsequently, to this solution, 30 g of pure water for swelling the sericin having been electrostatically bonded to the surfaces of the alumina-coated silica particles (II) was added with stirring the solution, and they were further stirred for 2 hours at room temperature. Thereafter, the stirring was terminated, and the solution was allowed to stand still for 18 hours at room temperature.

Next, the solid component contained in the standing liquid obtained as above was filtrated with a Buchner funnel in vacuo to obtain a cake-like substance. The cake-like substance was washed with 100 g (about 20 times the weight of the alumina-coated silica particles) of pure water.

Subsequently, the resulting cake-like substance was placed in a dryer maintained at a temperature of 60° C., dried for 4 hours and then subjected to vacuum drying in a desiccator maintained at room temperature. In order to disintegrate aggregates of the particles having been formed during drying, the dried substance was placed in a sample mill and crushed, whereby 4.78 g of a dry powder of alumina-coated silica particles to the surfaces of which sericin had been electrostatically bonded (referred to as "organic-inorganic composite particles (L)" hereinafter) was obtained.

Dispersibility of the thus obtained organic-inorganic composite particles (L) was evaluated by the aforesaid dispersibility evaluation method, and as a result, it was 8.63 μm.

Subsequently, the organic-inorganic composite particles (L) were subjected to the aforesaid differential thermal method (TG-DTA method), and as a result, a peak of a large amount of a water component, which was not detected from the surface of the base material (alumina-coated silica particles), was observed on the surfaces (areas where sericin had been electrostatically bonded) of the organic-inorganic composite particles.

Example 13

Preparation of Organic-Inorganic Composite Particles (M)

In a 300 ml glass beaker having a magnetic stirrer therein, 3.64 g of sericin (SILKGEN (registered trademark) G SOLUBLES-E available from Ichimaru Pharcos Co., Ltd., 5.5% by weight, average molecular weight: 5,500 to 40,000) was placed, and 16 g of ethanol was added so that the content of sericin might become about 1% by weight. Subsequently, with stirring the solution, acetone which was a solvent for bringing about molecular shrinkage of sericin was added to the solution so that the content of sericin might become about 0.3% by weight, and they were further stirred for 2 hours at room temperature. The amount of acetone added was 46 g.

Next, to the solution (containing sericin in the shrunken state) obtained as above, 5 g of the alumina-coated silica particles (II) prepared above were slowly added with stirring the solution, and they were further stirred for 2 hours at room temperature, whereby the sericin was electrostatically bonded to the surfaces of the alumina-coated silica particles (II).

Subsequently, to this solution, 60 g of pure water for swelling the sericin having been electrostatically bonded to the surfaces of the alumina-coated silica particles (II) was added with stirring the solution, and they were further stirred for 2 hours at room temperature. Thereafter, the stirring was terminated, and the solution was allowed to stand still for 18 hours at room temperature.

Next, the solid component contained in the standing liquid obtained as above was filtrated with a Buchner funnel in vacuo to obtain a cake-like substance. The cake-like substance was washed with 100 g (about 20 times the weight of the alumina-coated silica particles) of pure water.

Subsequently, the resulting cake-like substance was placed in a dryer maintained at a temperature of 60° C., dried for 4 hours and then subjected to vacuum drying in a desiccator maintained at room temperature. In order to disintegrate aggregates of the particles having been formed during drying, the dried substance was placed in a sample mill and crushed, whereby 4.80 g of a dry powder of alumina-coated silica particles to the surfaces of which sericin had been electrostatically bonded (referred to as "organic-inorganic composite particles (M)" hereinafter) was obtained.

Dispersibility of the thus obtained organic-inorganic composite particles (M) was evaluated by the aforesaid dispersibility evaluation method, and as a result, it was 9.95 µm.

Subsequently, the organic-inorganic composite particles (M) were subjected to the aforesaid differential thermal method (TG-DTA method), and as a result, a peak of a large amount of a water component, which was not detected from the surface of the base material (alumina-coated silica particles), was observed on the surfaces (areas where sericin had been electrostatically, bonded) of the organic-inorganic composite particles.

Example 14

Preparation of Organic-Inorganic Composite Particles (N)

In a 300 ml glass beaker having a magnetic stirrer therein, 0.05 g of hyaluronic acid (Hyaluronsan HA-LQ available from Kewpie Corporation, average molecular weight: 850,000 to 1,600,000) was placed, and 5 g of pure water was added so that the content of hyaluronic acid might become about 1% by weight. Then, they were stirred for 4 hours at room temperature to dissolve the hyaluronic acid in pure water. Subsequently, with stirring the solution, acetone which was a solvent for bringing about molecular shrinkage of hyaluronic acid was added to the solution so that the content of hyaluronic acid might become about 0.3% by weight, and they were further stirred for 2 hours at room temperature. The amount of acetone added was 12 g.

Next, to the solution (containing hyaluronic acid in the shrunken state) obtained as above, 5 g of titania particles (TIPAQUE WHITE (registered trademark) CR-50 available from Ishihara Sangyo Kaisha, Ltd., mean particle diameter measured by the measuring method A: 0.62 µm, mean particle diameter measured by the measuring method B: 13.37 µm) were slowly added with stirring the solution, and they were further stirred for 2 hours at room temperature, whereby the hyaluronic acid was electrostatically bonded to the surfaces of the titania particles.

Subsequently, to this solution, 25 g of pure water for swelling the hyaluronic acid having been electrostatically bonded to the surfaces of the titania particles was added with stirring the solution, and they were further stirred for 2 hours at room temperature. Thereafter, the stirring was terminated, and the solution was allowed to stand still for 18 hours at room temperature.

Next, the solid component contained in the standing liquid obtained as above was filtrated with a Buchner funnel in vacuo to obtain a cake-like substance. The cake-like substance was washed with 100 g (about 20 times the weight of the titania particles) of pure water.

Subsequently, the resulting cake-like substance was placed in a dryer maintained at a temperature of 60° C., dried for 4 hours and then subjected to vacuum drying in a desiccator maintained at room temperature. In order to disintegrate aggregates of the particles having been formed during drying, the dried substance was placed in a sample mill and crushed, whereby 4.76 g of a dry powder of titania particles to the surfaces of which hyaluronic acid had been electrostatically bonded (referred to as "organic-inorganic composite particles (N)" hereinafter) was obtained.

Dispersibility of the thus obtained organic-inorganic composite particles (N) was evaluated by the aforesaid dispersibility evaluation method, and as a result, it was 11.41 µm.

Subsequently, the organic-inorganic composite particles (N) were subjected to the aforesaid differential thermal method (TG-DTA method), and as a result, a peak of a large amount of a water component, which was not detected from the surface of the base material (titania particles), was observed on the surfaces (areas where hyaluronic acid had been electrostatically bonded) of the organic-inorganic composite particles. Moreover, a thermogravimetric change derived from hyaluronic acid was detected at around 400° C. though it was weak.

Example 15

Preparation of Organic-Inorganic Composite Particles (O)

In a 300 ml glass beaker having a magnetic stirrer therein, 0.2 g of hyaluronic acid (Hyaluronsan HA-LQ available from Kewpie Corporation, average molecular weight: 850,000 to 1,600,000) was placed, and 20 g of pure water was added so that the content of hyaluronic acid might become about 1% by weight. Then, they were stirred for 4 hours at room temperature to dissolve the hyaluronic acid in pure water. Subsequently, with stirring the solution, acetone which was a solvent for bringing about molecular shrinkage of hyaluronic acid was added to the solution so that the content of hyaluronic acid might become about 0.3% by weight, and they were further stirred for 2 hours at room temperature. The amount of acetone added was 46 g.

Next, to the solution (containing hyaluronic acid in the shrunken state) obtained as above, 5 g of titania particles (TIPAQUE WHITE (registered trademark) CR-50 available from Ishihara Sangyo Kaisha, Ltd., mean particle diameter measured by the measuring method A: 0.62 µm, mean particle diameter measured by the measuring method B: 13.37 µm) were slowly added with stirring the solution, and they were further stirred for 2 hours at room temperature, whereby the hyaluronic acid was electrostatically bonded to the surfaces of the titania particles.

Subsequently, to this solution, 60 g of pure water for swelling the hyaluronic acid having been electrostatically bonded to the surfaces of the titania particles was added with stirring the solution, and they were further stirred for 2 hours at room temperature. Thereafter, the stirring was terminated, and the solution was allowed to stand still for 18 hours at room temperature.

Next, the solid component contained in the standing liquid obtained as above was filtrated with a Buchner funnel in vacuo to obtain a cake-like substance. The cake-like substance was washed with 100 g (about 20 times the weight of the titania particles) of pure water.

Subsequently, the resulting cake-like substance was placed in a dryer maintained at a temperature of 60° C., dried for 4 hours and then subjected to vacuum drying in a desiccator maintained at room temperature. In order to disintegrate aggregates of the particles having been formed during drying, the dried substance was placed in a sample mill and crushed, whereby 4.76 g of a dry powder of titania particles to the surfaces of which hyaluronic acid had been electrostatically bonded (referred to as "organic-inorganic composite particles (O)" hereinafter) was obtained.

Dispersibility of the thus obtained organic-inorganic composite particles (O) was evaluated by the aforesaid dispersibility evaluation method, and as a result, it was 12.47 μm.

Subsequently, the organic-inorganic composite particles (O) were subjected to the aforesaid differential thermal method (TG-DTA method), and as a result, a peak of a large amount of a water component, which was not detected from the surface of the base material (titania particles), was observed on the surfaces (areas where hyaluronic acid had been electrostatically bonded) of the organic-inorganic composite particles. Moreover, a thermogravimetric change derived from hyaluronic acid was detected at around 400° C. though it was weak.

Comparative Example 1

Preparation of Inorganic Oxide Particles Having Cationic Surface Charge

In a 500 ml glass beaker having a magnetic stirrer therein, 20 g of silica particles (SILICA MICROBEADS (registered trademark) P-1500 available from JGC Catalysts and Chemicals Ltd., mean particle diameter measured by the measuring method A: 8.40 μm, mean particle diameter measured by the measuring method B: 26.37 μm) were placed, and 220 g of pure water was added so that the content of the solid component might become about 9% by weight. Next, a pH meter was installed in the glass beaker, and stirring was carried out at a rotational speed of 300 rpm for 2 hours using the magnetic stirrer to obtain a slurry of the silica particles.

Next, with stirring the resulting slurry at room temperature, a sodium hydroxide aqueous solution having a concentration of 15% was added to adjust pH of the slurry to about 12.0, and the slurry was stirred for 4 hours. Thereafter, the slurry was allowed to stand for 18 hours to electrostatically bond a sodium component to the surfaces of the silica particles.

Subsequently, the solid component contained in the slurry was filtrated with a Buchner funnel in vacuo. Then, washing with pure water of 400 g that is 20 times the weight of silica was carried out. Next, the resulting cake-like substance was dried at a temperature of 110° C. for 18 hours. In order to disintegrate aggregates of the particles having been formed during drying, the dried substance was crushed by a sample mill, whereby 20 g of a dry powder of silica particles (IV) coated with sodium (referred to as "sodium-coated silica particles" hereinafter) was obtained. The mean particle diameter of the thus obtained sodium-coated silica particles, as measured by the aforesaid measuring method A, was 9.68 μm.

Preparation of Organic-Inorganic Composite Particles (a)

In a 500 ml glass beaker having a magnetic stirrer therein, 0.480 g of hyaluronic acid (Hyaluronsan HA-LQ available from Kewpie Corporation, average molecular weight: 850,000 to 1,600,000) was placed, and 48 g of pure water was added so that the content of hyaluronic acid might become about 1% by weight. Then, they were stirred for 4 hours at room temperature to dissolve the hyaluronic acid in pure water. Subsequently, with stirring the solution, acetone which was a solvent for bringing about molecular shrinkage of hyaluronic acid was added to the solution so that the content of hyaluronic acid might become about 0.3% by weight, and they were further stirred for 2 hours at room temperature. The amount of acetone added was 144 g.

Next, to the solution (containing hyaluronic acid in the shrunken state) obtained as above, 12 g of the sodium-coated silica particles (IV) prepared above were slowly added with stirring the solution, and they were further stirred for 2 hours at room temperature, whereby the hyaluronic acid was electrostatically bonded to the surfaces of the sodium-coated silica particles (IV).

Subsequently, to this solution, 60 g of pure water for swelling the hyaluronic acid having been electrostatically bonded to the surfaces of the sodium-coated silica particles (IV) was added with stirring the solution, and they were further stirred for 2 hours at room temperature. Thereafter, the stirring was terminated, and the solution was allowed to stand still for 18 hours at room temperature.

Next, the solid component contained in the standing liquid obtained as above was filtrated with a Buchner funnel in vacuo to obtain a cake-like substance. The cake-like substance was washed with 240 g (about 20 times the weight of the sodium-coated silica particles) of pure water.

Subsequently, the resulting cake-like substance was placed in a dryer maintained at a temperature of 60° C., dried for 4 hours and then subjected to vacuum drying in a desiccator maintained at room temperature. In order to disintegrate aggregates of the particles having been formed during drying, the dried substance was placed in a sample mill and crushed, whereby 12.51 g of a dry powder of sodium-coated silica particles to the surfaces of which hyaluronic acid had been electrostatically bonded (referred to as "organic-inorganic composite particles (a)" hereinafter) was obtained.

Dispersibility of the thus obtained organic-inorganic composite particles (a) was evaluated, and as a result, it was 20.06 μm.

Subsequently, the organic-inorganic composite particles (a) were subjected to the aforesaid differential thermal method (TG-DTA method), and as a result, a peak of a large amount of a water component, which was not detected from the surface of the base material (sodium-coated silica particles), was not observed on the surfaces (areas where hyaluronic acid had been bonded) of the organic-inorganic composite particles. Moreover, even a weak thermogravimetric change derived from hyaluronic acid was not detected at around 400° C.

Comparative Example 2

Preparation of Organic-Inorganic Composite Particles (b)

In a 1 liter glass beaker having a magnetic stirrer therein, 0.20 g of hyaluronic acid (Hyalo-Oligo (registered trademark) available from Kewpie Corporation, average molecular weight: not more than 10,000) was placed, and 20 g of pure water was added so that the content of hyaluronic acid might become about 1% by weight. Then, they were stirred for 4 hours at room temperature to dissolve the hyaluronic acid in pure water. Subsequently, with stirring the solution, acetone which was a solvent for bringing about molecular shrinkage of hyaluronic acid was added to the solution so that the content of hyaluronic acid might become about 0.3% by weight, and they were further stirred for 4 hours at room temperature. The amount of acetone added was 60 g.

Next, to the solution (containing hyaluronic acid in the shrunken state) obtained as above, 5 g of the magnesium oxide-coated silica particles (III) prepared above were slowly added with stirring the solution, and they were further stirred for 2 hours at room temperature, whereby the hyaluronic acid was electrostatically bonded to the surfaces of the magnesium oxide-coated silica particles (III).

Subsequently, to this solution, 80 g of pure water for swelling the hyaluronic acid having been electrostatically bonded to the surfaces of the magnesium oxide-coated silica particles (III) was added with stirring the solution, and they were further stirred for 2 hours at room temperature. Thereafter, the stirring was terminated, and the solution was allowed to stand still for 18 hours at room temperature.

Next, the solid component contained in the standing liquid obtained as above was filtrated with a Buchner funnel in vacuo to obtain a cake-like substance. The cake-like substance was washed with 100 g (about 20 times the weight of the magnesium oxide-coated silica particles) of pure water.

Subsequently, the resulting cake-like substance was placed in a dryer maintained at a temperature of 60° C., dried for 4 hours and then subjected to vacuum drying in a desiccator maintained at room temperature. In order to disintegrate aggregates of the particles having been formed during drying, the dried substance was placed in a sample mill and crushed, whereby 5.3 g of a dry powder of magnesium oxide-coated silica particles to the surfaces of which hyaluronic acid had been electrostatically bonded (referred to as "organic-inorganic composite particles (b)" hereinafter) was obtained.

Dispersibility of the thus obtained organic-inorganic composite particles (b) was evaluated, and as a result, it was 19.36 µm.

Subsequently, the organic-inorganic composite particles (b) were subjected to the aforesaid differential thermal method (TG-DTA method), and as a result, a peak of a large amount of a water component, which was not detected from the surface of the base material (magnesium oxide-coated silica particles), was not observed on the surfaces (areas where hyaluronic acid had been bonded) of the organic-inorganic composite particles. Moreover, even a weak thermogravimetric change derived from hyaluronic acid was not detected at around 400° C.

In order to facilitate comparison, outlines of the organic-inorganic composite particles obtained above, that is, the example composite particles A to K and the comparative example composite particles a and b, are set forth in the following Table 1.

In Table 1, the coating ratio is defined as an amount of the raw material used in the preparation of the particles. That is to say, the coating ratio is defined as a proportion by weight of the cationic charge-imparting agent or the polymer gel for treating the inorganic metal oxide particles to the inorganic metal oxide particles which become the objects of preparation.

In Comparative Example 1, the particles wherein the surfaces of silica particles are modified with sodium are referred to as "sodium-coated silica particles" for convenience, but with regard to these particles, the same coating ratio as in other examples is not calculated.

In Comparative Example 1 and Comparative Example 2, a peak of a water component was not observed on the surfaces of the resulting particles a and b in the differential thermal method (TG-DTA method) evaluation. Moreover, a thermogravimetric change derived from hyaluronic acid was not detected. Therefore, the column for the component corresponding to the polymer gel is left blank.

TABLE 1

| Evaluation sample | Inorganic metal oxide particles | Cationic charge-imparting agent | Coating ratio (%) | Dispersed particle diameter (µm) | | Polymer gel molecules | | | | Dispersed particle diameter (µm) |
|---|---|---|---|---|---|---|---|---|---|---|
| | | | | Measuring method A | Measuring method B | Component | Molecular weight | Coating ratio (%) | Swelling step | Measuring method B |
| Example particles A | SiO$_2$ | Al$_2$O$_3$ | 5 | 8.60 | 23.17 | hyaluronic acid | 850,000-1,600,000 | 0.01 | ○ | 8.53 |
| Example particles B | SiO$_2$ | Al$_2$O$_3$ | 5 | 8.60 | 23.17 | hyaluronic acid | 850,000-1,600,000 | 0.04 | ○ | 8.59 |
| Example particles C | SiO$_2$ | Al$_2$O$_3$ | 2 | 10.42 | 26.37 | hyaluronic acid | 850,000-1,600,000 | 1 | ○ | 11.23 |
| Example particles D | SiO$_2$ | Al$_2$O$_3$ | 2 | 10.42 | 26.37 | hyaluronic acid | 850,000-1,600,000 | 4.0 | ○ | 10.33 |
| Example particles E | SiO$_2$ | Al$_2$O$_3$ | 2 | 10.42 | 26.37 | hyaluronic acid | 1,100,000-1,600,000 | 4.0 | ○ | 10.50 |
| Example particles F | SiO$_2$ | MgO | 10 | 8.26 | 28.67 | hyaluronic acid | 850,000-1,600,000 | 1.0 | ○ | 9.38 |
| Example particles G | SiO$_2$ | MgO | 10 | 8.26 | 28.67 | hyaluronic acid | 850,000-1,600,000 | 4.0 | ○ | 9.42 |
| Example particles H | SiO$_2$ | MgO | 10 | 8.26 | 28.67 | hyaluronic acid | 1,100,000-1,600,000 | 4.0 | ○ | 9.58 |
| Example particles I | SiO$_2$ | MgO | 10 | 8.26 | 28.67 | hyaluronic acid | 10,000 or less/850,000-1,600,000 | 4.0/4.0 | ○ | 9.59 |
| Example particles J | SiO$_2$ | Al$_2$O$_3$ | 2 | 10.42 | 26.37 | hyaluronic acid | 850,000-1,600,000 | 1.0 | x | 7.44 |
| Example particles K | SiO$_2$ | Al$_2$O$_3$ | 2 | 10.42 | 26.37 | hyaluronic acid | 850,000-1,600,000 | 4.0 | x | 8.59 |
| Example particles L | SiO$_2$ | Al$_2$O$_3$ | 2 | 10.42 | 26.37 | sericin | 5,500-40,000 | 1.0 | ○ | 8.63 |
| Example particles M | SiO$_2$ | Al$_2$O$_3$ | 2 | 10.42 | 26.37 | sericin | 5,500-40,000 | 4.0 | ○ | 9.95 |
| Example particles N | TiO$_2$ | — | | 0.67 | 11.37 | hyaluronic acid | 850,000-1,600,000 | 1.0 | ○ | 11.41 |

TABLE 1-continued

| Evaluation sample | Inorganic metal oxide particles | Cationic charge-imparting agent | Dispersed particle diameter (μm) | | Polymer gel molecules | | Coating ratio (%) | Swelling step | Dispersed particle diameter (μm) |
|---|---|---|---|---|---|---|---|---|---|
| | | Coating ratio (%) | Measuring method A | Measuring method B | Component | Molecular weight | | | Measuring method B |
| Example particles O | TiO$_2$ | — | 0.67 | 11.37 | hyaluronic acid | 850,000-1,600,000 | 4.0 | ○ | 12.47 |
| Comparative example particles a | SiO$_2$ | NaOH | — | 9.68 | | 850,000-1,600,000 | 4.0 | ○ | 20.06 |
| Comparative example particles b | SiO$_2$ | MgO | 10 | 8.26 | 28.67 | | 10,000 or less | 4.0 | ○ | 19.36 |

Example 16 and Comparative Example 3

Sensory Property of Organic-Inorganic Composite Particles

The powders of the organic-inorganic composite particles obtained in Examples 1 and 2 and Comparative Examples 1 and 2 were each subjected to an organoleptic test (sensory property evaluation test) by expert panelists, and with regard to three evaluation items of moistness, uniform spreadability and softness, hearing from the panelists was carried out. The results of the hearing were evaluated by the following evaluation score criteria. The results obtained in the evaluation test are set forth in Table 2.

The "SILICA MICROBEADS (registered trademark)" in the table indicates that a sample which had not been subjected to polymer gel treatment was used as a comparative example.

Evaluation Score Criteria
  AA: extremely excellent
  BB: excellent
  CC: average
  DD: inferior

TABLE 2

| Evaluation sample | Moistness | Softness | Uniform spreadability |
|---|---|---|---|
| Example cosmetic A | AA | BB | DD |
| Example cosmetic B | AA | BB | DD |
| Comparative example cosmetic a | CC | CC | CC |
| Comparative example cosmetic b | CC | CC | CC |
| SILICA MICROBEADS ® | CC | CC | CC |

SILICA MICROBEADS ® indicates that a sample which had not been subjected to polymer gel treatment was used.

Example 17 and Comparative Example 4

Preparation of Powder Foundation

The component (1) (described as "various beads" in Table 3), that is, any one of the example particles C to E obtained in Examples 3 to 5, respectively, and the comparative example particles a and b obtained in Comparative Examples 1 and 2, respectively, and the components (2) to (9) in Table 3 were placed in a mixer in blending ratios (% by weight) shown in Table 3, then stirred and homogeneously mixed. Next, the below-described cosmetic components (10) to (12) were placed in this mixer, then stirred and further homogeneously mixed.

Subsequently, the resulting cake-like substance was crushed. Thereafter, about 12 g of the crushed substance was taken out, then placed in an oblong metal plate of 46 mm×54 mm×4 mm and subjected to press molding.

Thus, example cosmetics C to E containing the example particles C to E, respectively, and comparative example cosmetics a and b containing the comparative example particles a and b, respectively, were obtained.

TABLE 3

Formulation of blended powder foundation

| | Cosmetic component to constitute powder foundation | Amount added (wt %) |
|---|---|---|
| 1 | Various beads | 5.0 |
| 2 | Talc | 34.0 |
| 3 | Sericite | 40.0 |
| 4 | Mica | 5.0 |
| 5 | Methylparaben | 0.2 |
| 6 | Titanium oxide | 7.0 |
| 7 | Yellow iron oxide | 1.2 |
| 8 | Red iron oxide | 0.4 |
| 9 | Black iron oxide | 0.2 |
| 10 | Dimethicone | 4.0 |
| 11 | Liquid paraffin | 2.0 |
| 12 | Glyceryl tri-2-ethylhexanoate | 1.0 |
| | | 100.0 |

Sensory Property of Powder Foundation in Use

The powder foundations containing the powders of the organic-inorganic composite particles were each subjected to an organoleptic test (sensory property evaluation test) by expert panelists, and with regard to three evaluation items of moistness, uniform spreadability and softness, hearing from the panelists was carried out. The results of the hearing were evaluated by the following evaluation score criteria. The results obtained in the evaluation test are set forth in Table 4.

The "SILICA MICROBEADS (registered trademark)" in the table indicates that a sample which had not been subjected to polymer gel treatment was used as a comparative example.

Evaluation Score Criteria
  AA: extremely excellent
  BB: excellent
  CC: average
  DD: inferior

TABLE 4

| Evaluation sample | Moistness | Softness | Uniform spreadability |
|---|---|---|---|
| Example particles C | BB | BB | DD |

TABLE 4-continued

| Evaluation sample | Moistness | Softness | Uniform spreadability |
|---|---|---|---|
| Example particles D | AA | BB | DD |
| Example particles E | AA | BB | DD |
| Example particles M | BB | BB | DD |
| Example particles O | BB | BB | DD |
| Comparative example particles a | CC | CC | DD |
| Comparative example particles b | CC | CC | DD |
| SILICA MICROBEADS ® | CC | CC | CC |

SILICA MICROBEADS ® indicates that a sample which had not been subjected to polymer gel treatment was used.

The invention claimed is:

1. A process for producing organic-inorganic composite particles comprising inorganic oxide particles each of which has a cationic charge on the particle surface and polymer gel molecules which are derived from a natural substance, have an anionic functional group and one or more hydroxyl groups in a molecule and further have water retention property due to shrinking and swelling property, said polymer gel molecules being electrostatically bonded to surfaces of the inorganic oxide particles, said process consisting of:
  (1) a step wherein a solvent capable of shrinking the polymer gel molecules is added to a solution containing the polymer gel molecules and they are stirred,
  (2) a step wherein the inorganic oxide particles are added to the solution obtained in the step (1) and they are stirred to electrostatically bond the polymer gel molecules to the surfaces of the inorganic oxide particles,
  (3) a step wherein a solvent capable of swelling the polymer gel molecules is added to the dispersion obtained in the step (2) and they are stirred to swell the polymer gel molecules having been electrostatically bonded to the surfaces of the inorganic oxide particles,
  (4) a step wherein the dispersion obtained in the step (3) is filtered to separate a solid component, and
  (5) a step wherein the solid component obtained in the step (4) is dried,
  wherein the polymer gel molecules are those of hyaluronic acid, the solvent
  added in step (1) is acetone, and the solvent added in step (3) is water.

2. The process for producing organic-inorganic composite particles as claimed in claim 1, wherein the polymer gel molecules are contained in an amount of 0.5 to 3.0% by weight in the solution in the step (1).

3. The process for producing organic-inorganic composite particles as claimed in claim 1, wherein the solvent capable of shrinking the polymer gel molecules is added to the solution in such a proportion that the content of the polymer gel molecules in the resulting solution becomes 0.2 to 1.0% by weight in the step (1).

4. The process for producing organic-inorganic composite particles as claimed in claim 1, wherein the stirring is carried out at a rate of 200 to 700 rpm at room temperature for 1 to 4 hours after the addition of the solvent capable of shrinking the polymer gel molecules in the step (1).

5. The process for producing organic-inorganic composite particles as claimed in claim 1, wherein the stirring is carried out at a rate of 200 to 700 rpm at room temperature for 1 to 6 hours after the addition of the inorganic oxide particles in the step (2).

6. The process for producing organic-inorganic composite particles as claimed in claim 1, wherein the solvent capable of swelling the polymer gel molecules is added so that the content of the polymer gel molecules in the resulting solution becomes 0.05 to 0.3% by weight in the step (3).

7. The process for producing organic-inorganic composite particles as claimed in claim 1, wherein the stirring is carried out at a rate of 200 to 700 rpm at room temperature for 1 to 6 hours after the addition of the solvent capable of swelling the polymer gel molecules in the step (3).

8. The process for producing organic-inorganic composite particles as claimed in claim 1, wherein the solid component is dried at normal pressure or under reduced pressure at a temperature of room temperature to 80° C. in the step (5).

* * * * *